(12) United States Patent
Hallinan et al.

(10) Patent No.: US 10,710,953 B2
(45) Date of Patent: Jul. 14, 2020

(54) METHOD FOR PURIFICATION OF GAA

(71) Applicant: LyondellBasell Acetyls, LLC, Houston, TX (US)

(72) Inventors: Noel C. Hallinan, Loveland, OH (US); David L. Ramage, Friendswood, TX (US); Daniel F. White, Houston, TX (US)

(73) Assignee: LyondellBasell Acetyls, LLC, Houston, TX (US)

(*) Notice: Subject to any disclaimer, the term of this patent is extended or adjusted under 35 U.S.C. 154(b) by 0 days.

(21) Appl. No.: 16/362,197

(22) Filed: Mar. 22, 2019

(65) Prior Publication Data

US 2019/0292123 A1 Sep. 26, 2019

Related U.S. Application Data

(60) Provisional application No. 62/647,355, filed on Mar. 23, 2018.

(51) Int. Cl.
- *C07C 51/12* (2006.01)
- *C07C 53/08* (2006.01)
- *C07C 51/47* (2006.01)

(52) U.S. Cl.
CPC .............. *C07C 51/12* (2013.01); *C07C 51/47* (2013.01); *C07C 53/08* (2013.01)

(58) Field of Classification Search
CPC .................................. C07C 51/12; C07C 53/08
See application file for complete search history.

(56) References Cited

U.S. PATENT DOCUMENTS

| | | |
|---|---|---|
| 5,932,764 A | 8/1999 | Morris et al. |
| 6,552,221 B1 | 4/2003 | Hallinan et al. |
| 7,223,886 B2 | 5/2007 | Scates et al. |
| 7,683,212 B2 | 3/2010 | Kojima et al. |
| 8,293,534 B2 | 10/2012 | Hallinan |
| 8,940,932 B2 | 1/2015 | Shimizu |
| 8,969,613 B2 | 3/2015 | Hallinan et al. |
| 9,056,825 B2 | 6/2015 | Torrence et al. |
| 9,216,936 B2 | 12/2015 | Torrence et al. |
| 9,561,994 B2 * | 2/2017 | Shaver ................. C07C 51/12 |
| 9,822,055 B2 | 11/2017 | Ramage et al. |
| 2008/0051601 A1 | 2/2008 | Sawyer et al. |
| 2014/0121404 A1 | 5/2014 | Hallinan et al. |
| 2016/0121320 A1 | 5/2016 | You et al. |
| 2016/0289153 A1 | 10/2016 | Scates et al. |
| 2016/0376213 A1 | 12/2016 | Ramage et al. |
| 2017/0158592 A1 | 6/2017 | Hallinan et al. |
| 2017/0158596 A1 | 6/2017 | Hallinan et al. |

FOREIGN PATENT DOCUMENTS

| | | |
|---|---|---|
| WO | 2008024198 A1 | 2/2008 |
| WO | 2014070739 A1 | 5/2014 |
| WO | 2017096235 A1 | 6/2017 |
| WO | 2017096255 A1 | 6/2017 |

OTHER PUBLICATIONS

The International Search Report and Written Opinion for PCT/US2019/023682 dated May 13, 2019.

* cited by examiner

*Primary Examiner* — Sikarl A Witherspoon

(57) ABSTRACT

A method comprising: contacting methanol with carbon monoxide in the presence of a liquid reaction medium under carbonylation conditions to form a carbonylation product comprising acetic acid; separating the carbonylation product into a liquid fraction and a vapor fraction comprising a majority of the acetic acid in the carbonylation product; removing, from the vapor fraction, water, light ends having a boiling point less than acetic acid, heavy ends having a boiling point greater than acetic acid, or a combination thereof, to yield a crude acetic acid product comprising at least 99.5 wt % acetic acid, less than or equal to 0.2 wt % water, and less than or equal to 2000 ppm oxidizable impurities, based on the total weight of the crude acetic acid product; and contacting the crude acetic acid product with an acidic ion exchange resin to provide a purified acetic acid product comprising less than 100 ppm oxidizable impurities.

20 Claims, 3 Drawing Sheets

METHOD FOR PURIFICATION OF GAA

CROSS-REFERENCE TO RELATED APPLICATIONS

This application claims the benefit of priority to U.S. Provisional Patent Application No. 62/647,355, filed on Mar. 23, 2018, which is incorporated herein by reference in its entirety.

TECHNICAL FIELD

This disclosure relates to the production of acetic acid and related processes. More specifically, this disclosure relates to the removal of impurities within such processes. Still more specifically, this disclosure relates to the removal of oxidizable impurities from acetic acid product streams comprising low (e.g., parts per million (ppm)) levels of such impurities.

BACKGROUND

Carboxylic acids, such as acetic acid, may be commercially produced by alcohol carbonylation. Unfortunately, carbonylation processes often create unwanted byproducts. Significant energy has been devoted to the removal of such byproducts, including a variety of processes and techniques. However, such processes and techniques can be complicated and costly.

Permanganate time (PT) is a quality test used industry wide for glacial acetic acid (GAA). The PT test is utilized to determine the amount of oxidizable impurities present in a GAA product comprising low levels (e.g., less than or equal to 2000 ppm) of oxidizable impurities. Oxidizable impurities or 'permanganate reducing compounds' (PRCs), include, without limitation, saturated and unsaturated carbonyl compounds including acetaldehyde, acetone, crotonaldehyde, 2-ethyl crotonaldehyde and associated aldol condensation products. Some methods attempt removal of permanganate reducing compounds from decanter light or heavy phases via techniques such as oxidation or multiple distillation and/or aqueous extraction. Others describe removal of such compounds via pressure distillation or the addition of extra distillation columns. Other methods involve utilizing permanganate itself as a reducing agent in the process, whereby the addition of aqueous or silica-supported $KMnO_4$ to the bottom of a distillation column is employed to remove oxidizable impurities such as acetaldehyde and crotonaldehyde. In addition to removal methods, various control methods that seek to limit the formation of acetaldehyde in the carbonylation reactor have been proposed. Some such methods indicate a possible 25% improvement in permanganate time of a so-produced GAA product.

Conventional systems and methods for the removal of oxidizable impurities/PRCs from carboxylic acids can be costly and time consuming. Accordingly, a need exists for improved systems and methods for enhancing the permanganate time of GAA without the need for conventionally employed removal methods and the drawbacks associated therewith. Disclosed herein are embodiments directed to providing such systems and methods.

SUMMARY

Herein disclosed is a method comprising: contacting methanol with carbon monoxide in the presence of a liquid reaction medium under carbonylation conditions to form a carbonylation product comprising acetic acid; separating the carbonylation product into a liquid fraction and a vapor fraction comprising a majority of the acetic acid in the carbonylation product; removing, from the vapor fraction, water, light ends having a boiling point less than that of acetic acid, heavy ends having a boiling point greater than that of acetic acid, or a combination thereof, to yield a crude acetic acid product comprising at least 99.5, 99.7, or 99.9 wt % acetic acid, less than or equal to 0.2, 0.15, or 0.1 wt % water, and less than or equal to 2000, 1000, or 750 ppm oxidizable impurities, based on the total weight of the crude acetic acid product; and contacting the crude acetic acid product with an acidic ion exchange resin to provide a purified acetic acid product comprising less than 100, 50, or 10 ppm oxidizable impurities.

Also disclosed herein is a method of removing oxidizable impurities from a crude acetic acid comprising greater than or equal to 99.5, 99.7, or 99.9 weight percent (wt %) acetic acid, less than or equal to 0.2, 0.15, or 0.1 wt % water, and from 10 to 2000, from 50 to 2000, or from 100 to 2000 ppm oxidizable impurities, the method comprising: contacting the crude acetic acid with a strongly acidic ion exchange resin to produce a purified acetic acid comprising less than or equal to 100, 50, or 10 ppm oxidizable impurities.

Also disclosed herein is a system for producing acetic acid, the system comprising: a carbonylation reactor for contacting methanol with carbon monoxide in the presence of a liquid reaction medium under carbonylation conditions to form a carbonylation product comprising acetic acid; a flash vessel operable to separate the carbonylation product into a liquid fraction and a vapor fraction comprising a majority of the acetic acid in the carbonylation product; one or more separation apparatus configured for removing, from the vapor fraction, water, light ends having a boiling point less than that of acetic acid, heavy ends having a boiling point greater than that of acetic acid, or a combination thereof, to yield a crude acetic acid product comprising at least 99.5, 99.7, or 99.9 wt % acetic acid, less than or equal to 0.2, 0.15, or 0.1 wt % water, and less than 2000, 1000, or 750 ppm oxidizable impurities; and an ion exchange column comprising an acidic ion exchange resin, located downstream of the one or more separation apparatus, and operable to reduce an amount of the oxidizable impurities in the crude acetic acid product by at least 30, 40, 50, 60, 70, 80, 85, 90, 95, or 98% and provide a purified acetic acid product comprising less than 100, 50, or 10 ppm oxidizable impurities.

While multiple embodiments are disclosed, still other embodiments will become apparent to those skilled in the art from the following detailed description. As will be apparent, certain embodiments, as disclosed herein, are capable of modifications in various aspects without departing from the spirit and scope of the claims as presented herein. Accordingly, the detailed description hereinbelow is to be regarded as illustrative in nature and not restrictive.

BRIEF DESCRIPTION OF THE DRAWINGS

The following figures illustrate embodiments of the subject matter disclosed herein. The claimed subject matter may be understood by reference to the following description taken in conjunction with the accompanying figures, in which:

DETAILED DESCRIPTION

Figure 1:
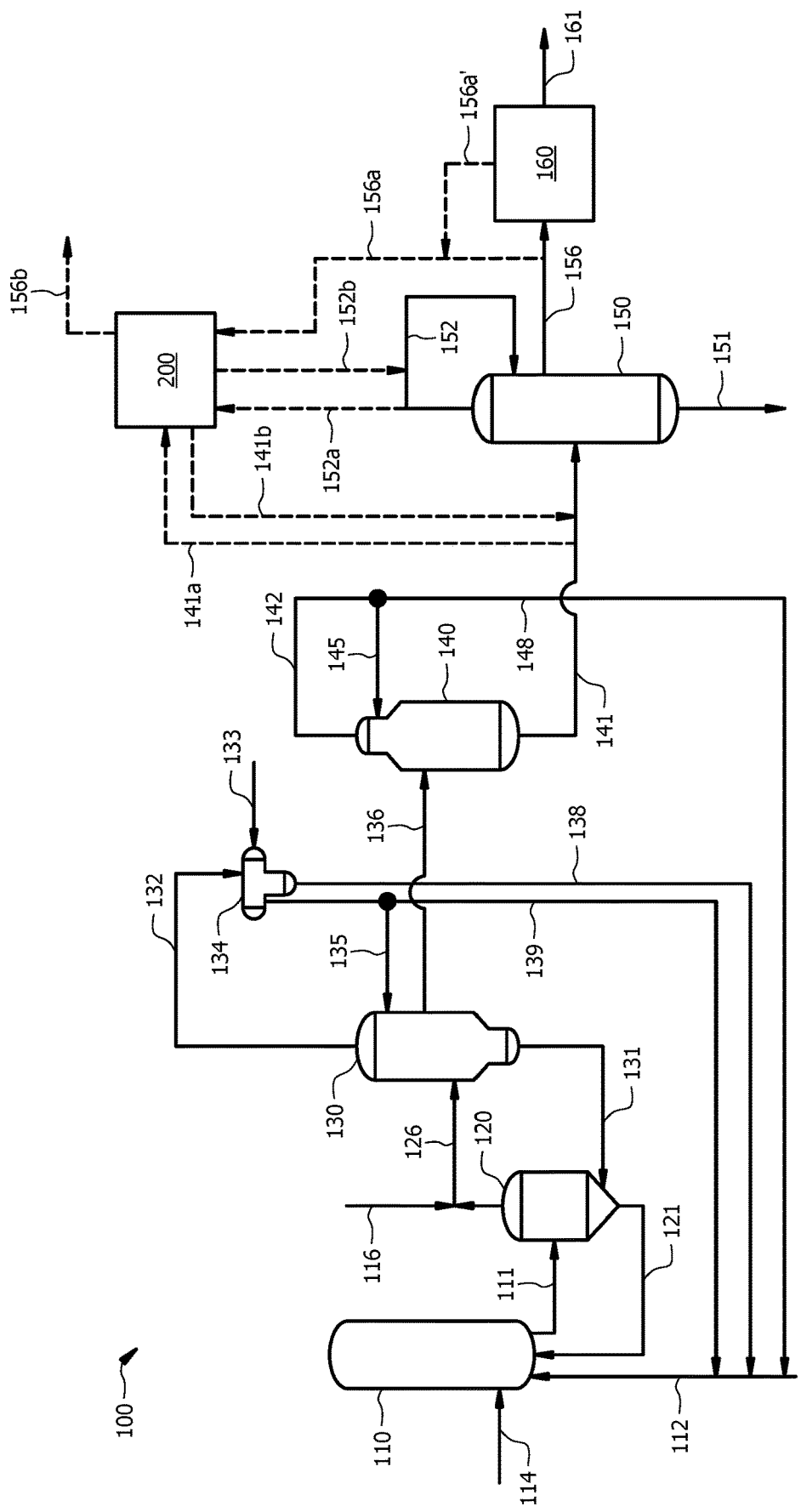
FIG. 1 is a schematic of a carboxylic acid production system 100, according to an embodiment of this disclosure.

This disclosure relates to systems and methods for the removal of oxidizable impurities from a carboxylic acid product via contact thereof with an acidic ion exchange resin. The terms 'oxidizable impurities' and 'permanganate reducing compounds' (or 'PRCs') are used interchangeably herein. In embodiments, the carboxylic acid is glacial acetic acid. Embodiments described herein thus include processes for producing acetic acid. Furthermore, embodiments include production of glacial acetic acid (which is encompassed by the term "acetic acid" as referenced herein). Glacial acetic acid refers to acetic acid that is often undiluted (e.g., includes a water concentration of less than or equal to 0.15 wt % based on the total weight of acetic acid and water). In embodiments, the acetic acid production processes may include carbonylation processes. For example (and for purposes of discussion herein), the acetic acid production processes may include the carbonylation of methanol and/or its derivatives to produce acetic acid. Thus, while suitable for removing oxidizable impurities from various carboxylic acid product streams, description will be made hereinbelow with reference to the removal of oxidizable impurities from glacial acetic acid (GAA) products.

The GAA contacted with the ion exchange resin as per this disclosure may be referred to herein as a crude or 'partially purified' acetic acid product. Although referred to as a 'crude' acetic acid, the method as described herein can generally be employed to remove impurities from a partially purified acetic acid product. Indeed, in embodiments, the contacting of the crude acetic acid with the ion exchange resin as described herein can be a final purification step or one of the final purification steps in the production of the acetic acid. In embodiments, the contacting of the crude acetic acid with the ion exchange resin as described herein can be a penultimate purification step in the production of the acetic acid. Thus, in embodiments, the crude acetic acid stream treated via acidic ion exchange as per this disclosure has been largely purified except for this penultimate or ultimate ion exchange purification step.

In embodiments, the crude carboxylic acid (e.g., acetic acid) process stream treated according to this disclosure can comprise at least 99, 99.5, 99.6, 99.7, 99.8, or 99.9 wt % carboxylic acid (e.g., acetic acid) and less than or equal to 0.2, 0.15, or 0.1 wt % water. The crude carboxylic acid (e.g., acetic acid) can comprise oxidizable impurities to be selectively removed via the ion exchange resin, and, in embodiments, can comprise less than or equal to 2000, 1500, 1000, or 750 ppm of such oxidizable impurities, based on the total weight of the crude carboxylic acid (e.g., acetic acid) process stream to be treated, in embodiments. The purified carboxylic acid (e.g., acetic acid) obtained via ion exchange treatment according to this disclosure can comprise at least 99, 99.5, 99.6, 99.7, 99.8, or 99.9 wt % carboxylic acid (e.g., acetic acid), less than or equal to 0.2, 0.15, or 0.1 wt % water, and/or less than or equal to 100, 90, 80, 70, 60, 50, 40, 30, 20, or 10 ppm of such oxidizable impurities. The amount of oxidizable impurities may be determined via gas chromatography (GC) and/or UV/Vis, for example as described hereinbelow.

The oxidizable impurities can comprise saturated carbonyl compounds, unsaturated carbonyl compounds, aldol condensation products thereof, propionic acid, or combinations thereof. In embodiments, the oxidizable impurities comprise acetaldehyde, acetone, methyl ethyl ketone, butyraldehyde, crotonaldehyde, 2-ethyl crotonaldehyde, 2-ethyl butyraldehyde, aldol condensation products thereof, propionic acid, or combinations thereof. In embodiments, the oxidizable impurities or PRCs include, without limitation, acetaldehyde, acetone, methyl ethyl ketone, butyraldehyde, crotonaldehyde, 2-ethyl crotonaldehyde, 2-ethyl butyraldehyde, aldol condensation products thereof, or combinations thereof. In embodiments, based on the weight thereof, the crude acetic acid product comprises from 0 ppm to 200 ppm, from 100 ppm to 200 ppm, or from 150 ppm to 200 ppm permanganate reducing compounds (PRCs).

Illustrative embodiments of the subject matter claimed below will now be disclosed. In the interest of clarity, not all features of an actual implementation are described in this specification. It will be appreciated that in the development of any such actual embodiment, numerous implementation-specific decisions can be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations disclosed herein is to be understood to set forth every number and range encompassed within the broader range of values. It is to be noted that the terms "range" and "ranging" as used herein generally refer to a value within a specified range and encompasses all values within that entire specified range. As used herein, a 'majority' refers to greater than 50 weight percent.

Further, in the description below, unless otherwise specified, the compounds described herein may be substituted or unsubstituted and the listing of compounds may include derivatives thereof.

The crude acetic acid treated according to the herein-disclosed system and method comprising acidic ion exchange can be produced via any systems and methods known in the art. Description of a system and method of this disclosure will now be made with reference to FIG. 1, which illustrates a schematic of a specific, non-limiting embodiment of a carboxylic acid production system 100 comprising an acidic ion exchanger 200 and exemplary apparatus for producing the crude acetic acid stream to be treated therein.

Carboxylic acid production system 100 comprises a reactor 110, a flash vessel 120, equipment associated with the reactor 110 and flash vessel 120, and streams associated with the reactor 110 and the flash vessel 120, for example, streams (or portions of streams) 111, 112, 114, 121, 126, 131, 116, 138, 139 and 148. Reactor 110 is a reactor or vessel in which an alcohol is carbonylated in the presence of a carbonylation catalyst to form a carboxylic acid at elevated pressure and temperature. Flash vessel 120 is a tank or vessel in which a reaction mixture obtained in the reactor, for example reactor 110, is at least partially depressurized and/or cooled to form a vapor stream and a liquid stream.

A carboxylic acid production system may further comprise a light-ends column 130, equipment associated with light-ends column 130, such as decanter 134, and streams associated with the light-ends column 130 and/or decanter 134, such as, for example, streams 116, 126, 131, 132, 133, 135, 136, 138 and 139. Light-ends column 130 is a fractioning or distillation column and includes any equipment associated with the column, including but not limited to heat exchangers, decanters, pumps, compressors, valves, and the like.

A carboxylic acid production system may further comprise a drying column 140, a heavy-ends column 150, equipment associated with drying column 140 and/or heavy-ends column 150, and streams associated with drying column 140 and heavy-ends column 150. For example, carboxylic acid production system 100 comprises drying column 140, heavy-ends column 150 and streams 136, 141, 142, 145, 148, 151, 152 and 156. Heavy-ends column 150 can be a fractioning or distillation column and includes any equipment associated with the column, including but not limited to heat exchangers, decanters, pumps, compressors and valves.

A carboxylic acid production system may further comprise an organic iodide-removal apparatus 160, and equipment and streams associated with same. For example, carboxylic acid production system 100 comprises organic iodide-removal apparatus 160 and streams 156 and 161.

A carboxylic acid production system may include process streams recycled to reactor 110, flash vessel 120, light-ends column 130, and/or decanter 134, such as, for example, streams 121, 138, 139 and 148.

The carbonylation processes utilized to produce acetic acid within reactor 110 may include reacting an alcohol, such as methanol and/or methanol derivative(s), with carbon monoxide in the presence of a reaction medium, such as a liquid reaction medium, under carbonylation conditions sufficient to form a carbonylation product including acetic acid, and recovering the formed acetic acid from the carbonylation product. In embodiments, reactor 110 may thus be configured to receive a carbon monoxide feed stream 114 and a methanol or methanol/methyl acetate feed stream 112. A reaction mixture may be withdrawn from reactor 110 via stream 111. Other streams may be included, for example, a stream that may recycle a bottoms mixture of reactor 110 back into reactor 110, or a stream may be included to release a gas from reactor 110. Stream 111 may include at least a part of the reaction mixture.

As described herein, the term "liquid reaction medium" refers to a reaction medium that is primarily liquid in form. For example, the liquid reaction medium contains minor amounts of alternative phases. In one or more embodiments, the liquid reaction medium is at least 90%, or at least 91%, or at least 92%, or at least 93%, or at least 94%, or at least 95%, or at least 96%, or at least 97%, or at least 98%, or at least 99% liquid phase.

The reaction medium includes a carbonylation catalyst. Carbonylation catalysts may include, but are not limited to, rhodium catalysts, iridium catalysts and palladium catalysts. Rhodium catalysts may include rhodium metal and rhodium compounds selected from rhodium salts, rhodium oxides, rhodium acetates, rhodium phosphates, organo-rhodium compounds, coordination compounds of rhodium or combinations thereof (See, for example, U.S. Pat. No. 5,817,869, which is hereby incorporated herein in its entirety for purposes not contrary to this disclosure). Iridium catalysts may include iridium metal and iridium compounds selected from iridium acetates, iridium oxalates, iridium acetoacetates or combinations thereof (See, for example, U.S. Pat. No. 5,932,764, which is hereby incorporated herein in its entirety for purposes not contrary to this disclosure).

In embodiments, the carbonylation catalyst is a transition metal catalyst, such as a rhodium catalyst. It is contemplated that any rhodium carbonylation catalyst may be used in the carbonylation process described herein. In embodiments, the rhodium catalyst comprises a rhodium source selected from rhodium metal, rhodium halides, rhodium oxide, rhodium acetate, organo-rhodium compounds, coordination compounds of rhodium, or similar rhodium compounds. Additionally, mixtures of different rhodium sources may also be used. Non-limiting examples of rhodium sources which can be used in the carbonylation process include $RhCl_3$, $RhBr_3$, $RhI_3$, $RhCl_3 \cdot 3H_2O$, $RhBr_3 \cdot 3H_2O$, $RhI_3 \cdot 3H_2O$, $Rh_2(CO)_4Cl_2$, $Rh_2(CO)_4Br_2$, $Rh_2(CO)_4I_2$, $Rh_2(CO)_8$, $Rh(CH_3CO_2)_2$, $Rh(CH_3CO_2)_3$, $Rh[(C_6H_5)_3P]_2(CO)I$, $Rh[(C_6H_5)_3P]_2(CO)Cl$, elemental Rh, $Rh(NO_3)_3$, $Rh(SnCl_3)[(C_6H_5)P]_2$, $RhCl(CO)[(C_6H_5)As]_2$, $RhI(CO)[(C_6H_5)Sb]_2$, $Rh[(C_6H_5)_3P]_2(CO)Br$, $Rh[(n-C_4H_9)_3P]_2(CO)Br$, $Rh[(n-C_4H_9)_3P]_2(CO)I$, $RhBr[(C_6H_5)_3P]_3$, $RhI[(C_6H_5)_3P]_3$, $RhCl[(C_6H_5)_3P]_3$, $RhCl[(C_6H_5)_3P]_3H_2$, $[(C_6H_5)_3P]_3Rh(CO)H$, $Rh_2O_3$, $[Rh(C_3H_4)_2Cl]_2$, $K_4Rh_2Cl_2(SnCl_2)_4$, $K_4Rh_2Br_2(SnBr_2)_4$, $[H][Rh(CO)_2I_2]$, $K_4Rh_2I_2(SnI_2)_4$, and complexes of the formula $[Rh(CO)_2 X_2][Y]$, wherein X is a halide and Y is a proton, an alkali metal cation, or a quaternary compound of nitrogen, phosphorus, or arsenic, or is a similar rhodium complex. In embodiments, the rhodium source is $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, or $[H][Rh(CO)_2I_2]$. In embodiments, the rhodium source is $Rh(CH_3CO_2)_2$, $Rh(CH_3CO_2)_3$, or $[H][Rh(CO)_2I_2]$.

The rhodium compound or complex may be used in a concentration sufficient to achieve a reasonable amount of carbonylation or an effective rate of carbonylation. Without being bound by theory, excess amounts of the rhodium catalyst can lead to the undesired byproducts. Thus, the optimization of the rhodium catalyst is one factor which can directly impact the rate, amount, and yield of the carbonylation product. In a carbonylation process, the concentration of the rhodium catalyst that may be used is from 10 ppm to 10,000 ppm, including from 200 ppm to 1200 ppm and 400 ppm to 1000 ppm. These concentrations can also be expressed using molarity. In embodiments, the concentration is from $1 \times 10^{-4}$ M to $4 \times 10^{-2}$ M, from $2 \times 10^{-3}$ M to $1.2 \times 10^{-2}$ M and from $4 \times 10^{-2}$ M to $1 \times 10^{-2}$ M. In embodiments, the concentration of carbonylation catalyst in the reaction medium may be at least 7.5 millimolar (mmol) or may be in a range of 1 mmol to 100 mmol, or 2 mmol to 5 mmol, or 2 mmol to 75 mmol, or 5 mmol to 50 mmol, or 7.5 mmol to 25 mmol of catalyst per liter of reaction medium. While these concentrations are sufficient to cause carbonylation to proceed, higher concentrations may be used so long as such concentrations do not cause an unsatisfactory extent of byproducts.

In embodiments, the present disclosure relates to reactor streams or reactor effluents of a carbonylation process that is conducted in liquid phase or in gas phase. In embodiments, the carbonylation reaction contains one or more liquid components that may be selected from acetic acid, methanol, water, organic iodide (e.g., methyl iodide), methyl acetate or combinations thereof.

The reaction medium may include an alkyl acetate, such as methyl acetate, for example. The concentration of alkyl acetate in the reaction medium may be in a range of from 0.6 wt % to 36 wt %, from 2 wt % to 20 wt %, from 2 wt % to 16 wt %, from 3 wt % to 10 wt %, or from 2 wt % to 8 wt %, based on the total reaction medium weight. In embodiments, methyl acetate is formed in situ via esterification of methanol feed. In other embodiments methyl acetate is charged to the reactor as a co-feed along with methanol where methyl acetate may vary from 0% to 100% of the total feed. Those skilled in the art will appreciate that the steady state methyl acetate concentration in the reactor is a function of reactor conditions and is largely unrelated to its source (in situ generated or added in feed). In embodiments, the methyl acetate concentration is maintained to produce a mass ratio between methyl acetate and the rhodium catalyst from 1000:1 to 2:1, such as a ratio from 700:1 to 5:1 and from 275:1 to 14:1.

In embodiments, the reaction medium further includes one or more promoters. For example, the reaction medium may include an iodide promoter. The iodide promoter is an organic iodide such as methyl iodide. The concentration of such promoters in the reaction medium may be in a range of from 0.6 wt % to 36 wt %, from 4 wt % to 24 wt %, or from 6 wt % to 20 wt %, based on the total weight of the reaction medium. The iodide promoter may be introduced to the reaction medium in a form such that the introduced compound will directly promote the carbonylation reaction (e.g., introduction of methyl iodide to the carbonylation reaction). Alternatively, one or more compounds may be introduced to the reaction medium to form in-situ generated compounds capable of promoting the carbonylation reaction. For example, a carbonylation process may comprise introduction of hydrogen iodide to the reaction medium to form methyl iodide therefrom, which acts as a promoter. Thus, in embodiments, the reactor effluent or carbonylation product is produced from a carbonylation process which comprises a liquid medium and comprises an iodide source. In embodiments, the iodide source is methyl iodide or hydroiodic acid. In embodiments, the methyl iodide is added directly to the reaction mixture. In embodiments, the methyl iodide can be generated in situ from the reaction of hydroiodic acid with methanol. Without being bound by theory, it is believed that the methyl iodide oxidatively adds to the rhodium catalyst as the first step of the catalytic cycle.

A variety of different concentrations of the iodide source may be used in the carbonylation reaction of the present disclosure. In embodiments, the amount of methyl iodide added to the reaction comprises a concentration from 0.6 wt % to 36 wt % of the liquid reaction component, such as from 3.6 wt % to 24 wt % of the liquid reaction component. The amount of methyl iodide can also be determined as a molarity of the liquid reaction component. In embodiments, the concentration of methyl iodide is from 0.05 M to 3.0 M, including from 0.3 M to 2.0 M. In embodiments, hydroiodic acid is used as the iodide source. In embodiments, hydrogen iodide (HI) is used as the iodide source. In embodiments, the concentration of hydroiodic acid or hydrogen iodide used in the carbonylation reaction is from 0.6 wt % to 23 wt %, including from 2.3 wt % to 11.6 wt %. The concentration of the hydroiodic acid or hydrogen iodide can be measured as the molarity of the liquid reaction component. In embodiments, the concentration of hydroiodic acid or hydrogen iodide is from 0.05 M to 2.0 M, such as from 0.2 M to 1.0 M.

In embodiments, the carbonylation reaction further comprises adding a carboxylic acid to the liquid reaction component. In embodiments, the carboxylic acid is acetic acid. In embodiments, the concentration of acetic acid added to the liquid reaction component is in a range of from 20 wt % to 80 wt % or when measured in molarity from 3.0 M to 12.0 M, such as from 35 wt % to 65 wt % or when measured in molarity from 5 M to 10 M. In embodiments, the balance of the liquid reaction component is acetic acid.

In embodiments, the carbonylation catalyst is utilized with a co-catalyst. In such aspects, the carbonylation reaction can further comprise adding a second metal compound to the reaction mixture. In embodiments, the second metal is a transition metal or a post-transition metal. The co-catalyst may be selected from metals and metal compounds including osmium, rhenium, ruthenium, cadmium, mercury, zinc, gallium, indium, tungsten or combinations thereof. In embodiments, the metal compounds include metal acetates. In embodiments, the carbonylation reaction further comprises adding one or more compounds or complexes of a metal selected from ruthenium, rhenium, osmium, cadmium, zinc, mercury, gallium, indium, or tungsten or combinations thereof. In embodiments, any soluble or heterogeneous source of ruthenium can be added to the reaction mixture to enhance the yield and production of the carbonylation process. Some non-limiting examples of ruthenium compounds or complexes that can be used in the carbonylation reaction include ruthenium halides, ruthenium carbonyl, ruthenium oxides, ruthenium carboxylates, ruthenium carbonyl complexes, organoruthenium complexes such as tetrachlorobis(benzene)diruthenium(II), dichloro(cycloocta-1, 5-diene) ruthenium(II) polymer, or tetrachlorobis(4-cumene)diruthenium(II) or mixed ruthenium halocarbonyls compounds such as dichlorotricarbonylruthenium(III) dimers or dibromotricarbonyl-ruthenium(II) dimers.

In embodiments, the concentration of the second metal added to the liquid reaction component is added relative to the carbonylation catalyst. In embodiments, the amount of the second metal relative to the carbonylation catalyst is from 0.1:1 to 20:1, including from 0.5:1 to 10:1 and from 2:1 to 10:1. In embodiments, the second metal is added to the reaction medium at a concentration up to the limit of solubility of the second metal in the reaction mixture. In embodiments, the concentration of the second metal is less than 8000 ppm, including 400 ppm to 7000 ppm. In embodiments, the concentration of co-catalyst in the reaction medium may be in a range of from 500 ppm to 3000 ppm, or from 1000 ppm to 2000 ppm, based on the total reaction medium weight.

In embodiments, the carbonylation process further comprises water in the reaction mixture. In embodiments, the water is added deliberately to the reaction mixture. In embodiments, the water is a contaminant from the addition of other components. Without being bound by theory, the addition of water may promote the final conversion of the carbonylated compound into the appropriate carboxylic acid from the acid halide. In embodiments, the reaction medium thus further includes water. Based on the total weight of the reaction medium, the concentration of water in the reaction medium may be in a range of from 1 wt % to 14 wt %, from 1 wt % to 5 wt %, or from 4 wt % to 8 wt %, or less than or equal to 10 wt %, 8 wt %, or 6 wt %. The amount of water added to the reaction may be such that the concentration of water in the reaction medium is maintained in a range of from 1 wt % to 14 wt %, from 1 wt % to 5 wt %, or from 4 wt % to 8 wt %, or less than or equal to 10 wt %, 8 wt % or 6 wt %. The amount of water can, in embodiments, be measured relative to the amount of catalyst used in the reaction. In embodiments, the mass ratio of water to catalyst is from 0.5:1 to 4000:1, such as from 270:1 to 1750:1.

It is contemplated that a supplemental gas such as hydrogen may be supplied to the reaction medium. In embodiments, one of the gases added to the reaction mixture is hydrogen gas. Supplemental hydrogen may be supplied to the reaction medium to provide a total hydrogen concentration in the gaseous component of the feedstock to the carbonylation reaction in a range of from 0.1 mole percent (mol %) to 5 mol %, or from 0.3 mol % to 3 mol %. Without being bound by theory, the addition of hydrogen to the reaction mixture, particularly a reaction mixture comprising a rhodium catalyst, may decrease the selectivity of the carbonylation process favoring the production of byproducts such as aldehydes and alcohols. Furthermore, without being bound by theory, the carbonylation reactions which comprise hydrogen may exhibit increased catalytic efficacy. The amount of hydrogen gas utilized depends on the catalyst and other reactive metal components employed, as well as the identification of the desired products. In embodiments, the molar ratio of hydrogen relative to carbon monoxide (CO) in the reaction mixture is from 2:1 to 1:8, such as from 1:1 to 1:4. In embodiments, the concentration of the hydrogen added to the reaction mixture is from 0.1 mol % to 5 mol % based upon the amount of CO added to the reactor. In embodiments, the concentration of hydrogen is from 0.5 mol % to 3 mol %. In embodiments, the hydrogen gas is added to the reactor as a separate stream from the other gaseous components. In embodiments, the hydrogen gas is added as a mixture with CO. In embodiments, hydrogen gas can be added to the reaction mixture as needed in order to maintain a consistent concentration of hydrogen gas in the reaction mixture. As CO is consumed in the reaction, in embodiments, the molar ratio of hydrogen to CO can increase to a concentration from 1000:1 to 100:1. As the molar ratio of hydrogen to CO changes, in embodiments, more CO is added to the reaction mixture to increase the molar ratio of CO to hydrogen.

In embodiments, the carbonylation reaction comprises adding CO to the reaction mixture. In embodiments, the CO can be added as a gas. In embodiments, the CO is generated in situ from the ligands of one or more of the metal catalysts. In embodiments, CO is added at a pressure from 70 kPa to 5,600 kPa. In embodiments, CO is added at a pressure from 325 kPa to 3,500 kPa. In embodiments, CO is added at a pressure from 650 kPa to 2,100 kPa. In embodiments, the reaction comprises continuous addition of CO to the reaction mixture to maintain a constant molar ratio of CO as the CO is consumed in the reaction.

In embodiments, the present disclosure provides a carbonylation process which can be carried out using a wide variety of different reactor systems. In embodiments, the carbonylation process is carried out in a batch mode reactor. In embodiments, the carbonylation process is carried out in a continuous mode reactor. In embodiments, the carbonylation process is carried out in a fixed bed or fluidization reactor.

In embodiments, the carbonylation method of the present disclosure is conducted under an increased pressure. In embodiments, the reaction pressure is from 1350 kPa to 8,500 kPa, such as from 2,000 kPa to 4,200 kPa or 2,800 kPa. In embodiments the temperature of the carbonylation reaction is elevated above room temperature. In embodiments, the temperature of the carbonylation reaction is greater than 100° C., such as from 150° C. to 225° C., from 160° C. to 220° C., from 170° C. to 200° C. or 175° C.

The reaction effluent of the carbonylation process can include the use of a phosphine oxide in production of a carboxylic acid in an amount relative to the rhodium catalyst. It is contemplated that any amount of phosphine oxide may be used in the reaction process. In embodiments, the amount of phosphine oxide used is sufficient to stabilize the rhodium carbonylation catalyst, such as greater than 50 equivalents per equivalent of rhodium catalyst or greater than 100 equivalents per equivalent of rhodium catalyst. The amount of phosphine oxide used can also be described in terms of a concentration of the reaction mixture. In embodiments, the amount of phosphine oxide used is from 0.03 M to 2.25 M, such as from 0.4 M to 1.4 M. In embodiments, the concentration of the phosphine oxide is sufficient to achieve an improvement in some process metric such as increased rate, increased yield, or decreased production of one or more byproducts. Without being bound by theory, the addition of phosphine oxide may prevent the precipitation of the active rhodium catalyst and thus maintain the rate of the carbonylation reaction.

In embodiments, the carbonylation further comprises the addition of an iodide salt. It is contemplated that the iodide anion of the salt may be the relevant element for the carbonylation reaction and, as such, the identity of the cation may be less relevant. Thus, in embodiments, an iodide salt with any cation may be used in the carbonylation reaction described herein. In embodiments, the iodide salt is a metal iodide salt. In embodiments, the metal is a Group 1, Group 2, or transition metal cation. In embodiments, the metal is a Group 1 or Group 2 metal cation. In embodiments, the metal is an alkali metal cation. In embodiments, the iodide salt is an organic cation iodide. In embodiments, the organic cation is a quaternary organic cation. In embodiments, the quaternary organic cation comprises a positively charged quaternary nitrogen atom. The concentration of iodide salt which may be used in the carbonylation method varies widely and is dependent on the concentration of the reactive component. Without being bound by theory, the ratio of iodide salt to methyl acetate, methanol, dimethyl ether, or other reactive intermediates used within the carbonylation reaction affects the reaction rate. In embodiments, the concentration of the iodide salt is from 1 wt % to 30 wt % or from 0.075 M to 2.25 M, from 2 wt % to 20 wt % or from 0.075 M to 1.5 M or from 10 wt % to 20 wt % or from 0.75 M to 1.5 M. In embodiments, the molar ratio of the metal to the rhodium catalyst is greater than 38:1 or greater than 75:1. In embodiments, a molar ratio of the metal to the rhodium catalyst is sufficient to stabilize the rhodium catalyst.

In embodiments, the reaction conditions comprise using a low concentration of a metal iodide, such as less than or equal to 5, 4, 3, 2, or 0 wt %. In embodiments, the carbonylation is performed in the absence of a metal iodide. For example, in embodiments, the carbonylation is performed in the absence of a lithium source, such as lithium iodide, such that streams throughout (including, without limitation, the vapor fraction in vapor stream 126, the dried acetic acid process stream 141, the side drawn acetic acid process stream 136, the acetic acid process stream 156 withdrawn from heavy ends column 150, the crude acetic acid stream introduced into acidic ion exchanger 200 via, for example, stream 141a, 152a, or 156a, or a combination thereof, as described in detail hereinbelow) comprise less than or equal to 1, 5, or 50 ppm lithium. In embodiments, when a co-catalyst or promoter is added to the reaction, the concentration of the metal iodide is less than 3.5 wt %, including less than 3.0 wt %, less than 2.5 wt %, less than 2.0 wt % and less than 1.5 wt %. In embodiments, the concentration of metal iodide correlates to the total concentration of iodide in the reactor. In embodiments, the concentration of iodide in the reactor comprises iodide from the metal catalyst, metal co-catalysts or promoters, or the addition of a metal iodide. In embodiments, the concentration of iodide is measured by titrating $AgNO_3$ into a sample of the reaction media and measuring the amount of silver iodide that precipitates from the solution.

In practice, carbonylation reaction conditions vary depending upon reaction parameters, reactor size and charge and the individual components employed. However, in embodiments, the carbonylation process may be a batch or continuous process and the carbonylation conditions may include a carbonylation pressure in a range of from 200 pounds per square inch gauge (psig) (1379 kilopascals (kPa)) to 2000 psig (13790 kPa), from 200 psig (1379 kPa) to 1000 psig (6895 kPa), or from 300 psig (2068 kPa) to 500 psig (3447 kPa), and/or a carbonylation temperature in a range of from 150° C. to 250° C., from 170° C. to 220° C., or from 150° C. to 200° C.

The carbonylation product includes the formed acetic acid. In addition to the acetic acid, the carbonylation product may include one or more impurities. Impurities are defined herein as any component in a process stream other than the targeted product itself (e.g., acetic acid is the targeted product in the carbonylation product stream). For example, the impurities present in the carbonylation product stream may include water, propionic acid, aldehydes (e.g., acetaldehyde, crotonaldehyde, butyraldehyde and derivatives thereof), alkanes, formic acid, methyl formate, or combinations thereof, as well as additional compounds other than the acetic acid, depending on the specific process. As noted above and described in more detail hereinbelow, oxidizable impurities in various process streams can be removed via the system and method of this disclosure.

In one or more embodiments, components within the carbonylation product stream (or at least a portion thereof) may be separated from one another via flash separation into a liquid fraction and a vapor fraction. The liquid fraction may include residual carbonylation catalyst as well as other components, while the vapor fraction may include acetic acid, unreacted reactants, water, methyl iodide and impurities generated during the carbonylation reaction. For example, the vapor fraction may include acetic acid, water, methanol, methyl acetate, methyl iodide, acetaldehyde, or a combination thereof. The liquid fraction may be recycled to the carbonylation reaction while the vapor fraction may undergo supplemental separation, for example, as described hereinbelow.

For example, in the embodiment of FIG. 1, flash vessel 120 may be configured to receive carbonylation reaction product stream 111 from reactor 110. In flash vessel 120, stream 111 may be separated into a vapor stream 126 and a liquid stream 121. Vapor stream 126 may be communicated to a light-ends column 130, and liquid stream 121 may be communicated to reactor 110. In embodiments, vapor stream 126 may comprise acetic acid, water, methyl iodide, methyl acetate, HI, or a combination thereof, for example.

Flash vessel 120 may be operated at a pressure below that of reactor 110. In embodiments, flash vessel 120 may be operated at a pressure of from 10 psig to 100 psig. In embodiments, flash vessel 120 may be operated at a temperature of from 100° C. to 160° C.

Impurities are often separated from the acetic acid prior to use of the acetic acid in subsequent processes, such as industrial processes. Such separation processes may include those available in the relevant literature and may include separating one or more of the impurities from the acetic acid within a process stream (wherein the process stream may be referred to as "impure acetic acid") to form a more pure acetic acid. Such separation processes may be performed as described in the art, for example via one or more methods including, but not limited to, extraction, distillation, extractive distillation, caustic treatment, scavenging, adsorption or a combination thereof. Such separation processes can be utilized to provide, from the vapor stream 126, a crude acetic acid product treated via acidic ion exchange as per this disclosure to reduce the amount of oxidizable impurities therein. As used herein, the term "more pure acetic acid" refers to an acetic acid stream having a concentration of one or more impurities that is reduced in comparison to the concentration of that impurity in an upstream feed stream. It is to be noted that use of the term "acetic acid process stream" herein refers to any stream containing the majority of the produced acetic acid.

The supplemental separation may include a first distillation column (e.g., a light ends distillation column) adapted to separate components of the vapor fraction and form a first distillation column overhead stream (also referred to as a light ends overhead stream), an acetic acid stream, and a first distillation column bottoms stream (also referred to as a light ends bottoms stream). The acetic acid stream may comprise primarily acetic acid and water, and may be extracted as a side draw from light ends distillation column 130, in embodiments. The light ends overhead stream may comprise methyl iodide, water, methanol, methyl acetate, impurities or combinations thereof. For example, the light ends overhead can comprise methyl iodide, water, methyl acetate, acetic acid, acetaldehyde, or a combination thereof.

In the embodiment of FIG. 1, light-ends distillation column 130 may include a distillation column and equipment associated with the distillation column including but not limited to a heat exchanger, a decanter 134, pumps, compressors, valves, and other related equipment. Light-ends column 130 may be configured to receive vapor stream 126 from flash vessel 120. First or light-ends overhead stream 132 includes overhead product from light-ends column 130, and light-ends bottoms stream 131 includes bottoms product from light-ends column 130. Light-ends bottoms stream 131 may recycle light ends bottoms to flash vessel 120, in embodiments. Stream 136 may extract acetic acid product (e.g., as a side draw) from light-ends column 130. Other streams may be included, for example, a stream that may recycle a bottoms mixture of light-ends column 130 back into the light-ends column 130. Any stream received by or emitted from the light-ends column 130 may pass through a pump, compressor, heat exchanger, and the like as is common in the relevant art. Light-ends column 130 may include a decanter 134, and light-ends overhead stream 132 may pass into decanter 134.

In embodiments, light-ends column 130 may comprise at least 10 theoretical stages or 16 actual stages. In embodiments, light-ends column 130 may comprise at least 14 theoretical stages. In embodiments, light-ends column 130 may comprise at least 18 theoretical stages. In embodiments, one actual stage may equal approximately 0.6 theoretical stages. Actual stages can be trays or packing. The reaction mixture may be fed via vapor stream 126 to light-ends column 130 at the bottom or the first stage of light-ends column 130.

Light-ends overhead stream 132 may include acetaldehyde, water, carbon monoxide, carbon dioxide, methyl iodide, methyl acetate, methanol and acetic acid, or a combination thereof. Light-ends bottoms stream 131 may include acetic acid, methyl iodide, methyl acetate, HI, water, or a combination thereof. Acetic acid process stream 136 may include acetic acid, HI, water, heavy impurities, or a combination thereof.

In embodiments, light-ends column 130 may be operated at an overhead pressure within the range of 20 psia (1.4 kg/cm$^2$) to 50 psia (3.5 kg/cm$^2$), alternatively, the overhead pressure may be within the range of 30 psia (2 kg/cm$^2$) to 35 psia (2.5 kg/cm$^2$). In embodiments, light-ends column 130 may be operated at an overhead temperature within the range of 95° C. to 150° C., alternatively, the overhead temperature may be within the range of 110° C. to 150° C., alternatively, the overhead temperature may be within the range of 125° C. to 150° C. In embodiments, light-ends column 130 may be operated at a bottom pressure within the range of 25 psia (1.8 kg/cm$^2$) to 45 psia (3.2 kg/cm$^2$), alternatively, the bottom pressure may be within the range of 30 psia (2.1 kg/cm$^2$) to 50 psia (3.5 kg/cm$^2$). In embodiments, light-ends column 130 may be operated at a bottom temperature within the range of 115° C. to 170° C., alternatively, the bottom temperature is within the range of 125° C. to 150° C. In embodiments, acetic acid process stream 136 may be emitted from light-ends column 130 as a liquid side draw. Stream 136 may be operated at a pressure within the range of 25 psia (1.8 kg/cm$^2$) to 45 psia (3.2 kg/cm$^2$), alternatively, the pressure may be within the range of 30 psia (2.1 kg/cm$^2$) to 50 psia (2.8 kg/cm$^2$). In embodiments, the temperature of stream 136 may be within the range of 90° C. to 140° C., alternatively, the temperature may be within the range of 125° C. to 135° C. Stream 136 may be taken between the fifth to the eighth actual stage of light-ends column 130.

The first overhead stream may be condensed and separated in a decanter to form, relative to each phase, a "light" aqueous phase and a "heavy" organic phase. The heavy organic phase may include methyl iodide and aldehyde impurities. All or a portion of the heavy organic phase may be recycled to reactor 110. The light aqueous phase may include water, aldehyde impurities, acetic acid, methyl acetate, impurities, or a combination thereof. All or a portion of the light aqueous phase may be recycled to reactor 110 or light-ends distillation column 130. In the embodiment of FIG. 1, decanter 134 is configured for the separation of a light aqueous phase extracted therefrom via light aqueous phase decanter outlet stream 135 from a heavy organic phase extracted therefrom via heavy organic phase decanter outlet stream 138.

Stream 135 may emit from decanter 134 and recycle a portion of the light aqueous phase from decanter 134 back to light-ends column 130. Stream 138 may emit from decanter 134 and may recycle at least a portion of the heavy organic phase back to reactor 110 via, for example, stream 112 or be may combined with any of the other streams that feed the reactor. Stream 139 may recycle a portion of the light aqueous phase of decanter 134 back to reactor 110 via, for example, stream 112.

In embodiments, at least a portion the light organic phase, at least a portion of the heavy organic phase, or a combination thereof is subjected to further distillation and/or extraction (e.g., water extraction) to further remove impurities therefrom prior to recycle to reactor 110 (for example, via streams 138 and/or 139), to light-ends column 130 (for example, via stream 135), or both. For example, impurities may be removed from the heavy organic phase extracted from decanter 134 via stream 138 by contact with a silicoaluminophosphate (SAPO) as described in U.S. Patent App. No. 2017/0158592, and/or 2017/0158596; impurities may be removed from the heavy organic phase extracted from decanter 134 via stream 138 by contact with a resin or a liquid methanesulfonic acid (MSA) catalyst, as described in U.S. Pat. No. 8,969,613; impurities may be removed from the light aqueous phase and the heavy organic phase from decanter 134 via distillation and extraction as described in U.S. Pat. No. 8,940,932; impurities may be removed from the light aqueous phase extracted from decanter 134 via light aqueous phase decanter outlet stream 135 by various combinations of distillation and extraction thereof, as described in U.S. Pat. Nos. 7,223,886; 9,056,825; and/or 9,216,936. The disclosure of each of the aforementioned patents and patent applications are hereby incorporated herein by reference for purposes not contrary to this disclosure.

The heavy, organic phase in heavy organic phase decanter outlet stream 138 may comprise acetaldehyde, methyl iodide (MeI), methyl acetate, hydrocarbons, acetic acid, water, or a combination thereof. In embodiments, stream 138 may be essentially non-aqueous with a water concentration of less than 1 wt %. In embodiments, stream 138 may comprise MeI greater than 50% by weight of the stream. The light, aqueous phase in streams 135 and 139 may comprise water (e.g., greater than 50% by weight of the stream), acetic acid, methyl acetate, methyl iodide and acetic acid, or a combination thereof. Make-up water may be introduced into decanter 134 via stream 133.

In embodiments, oxidizable impurities are removed from all or a portion of the light aqueous phase, an aqueously extracted heavy organic phase, (and/or from all or a portion of a drying column water stream 142 described hereinbelow), or a combination thereof via an adsorbent vessel 210. In such embodiments, all or a portion of the light aqueous phase 139, and/or all or a portion of an aqueous solution resulting from aqueous extraction of the heavy organic phase 138 (and/or all or a portion of a drying column water stream 142) may be introduced into an adsorbent vessel comprising an adsorbent (which may have a molar ratio of Si/Al greater than 30 and/or a particle size of less than 10 microns) selected from nanozeolites, zeolites, acidic ion exchangers, silicates, or a combination thereof for removal of oxidizable impurities therefrom prior to recycle (e.g., recycle to carbonylation reactor 110, drying column 140, etc.).

The acetic acid process stream 136 may be passed to a drying column, as described further hereinbelow, to remove any water contained therein. The drying column may comprise a vessel and equipment associated with the vessel including but not limited to heat exchangers, decanters, pumps, compressors, valves, and the like. In the embodiment of FIG. 1, carbonylation system 100 comprises drying column 140 configured to receive acetic acid process stream 136 from light-ends column 130 and remove water therefrom. Drying column 140 may separate components of stream 136 into drying column water stream 142 and dried acetic acid process stream 141.

Stream 142, comprising drying column water, may emit from drying column 140, recycle back to drying column 140 via stream 145, and/or recycle back to reactor 110 via stream 148 (via, for example, stream 112). Stream 141 may emit from the drying column 140 and may include de-watered or 'dried' acetic acid product. In embodiments, the side draw acetic acid process stream 136 comprises greater than or equal to 2, 5, or 10 wt % water, and the dried acetic acid process stream 141 can comprise less than or equal to 5000, 1000, or 500 ppm water. In embodiments, at least a portion 141a of dried acetic acid process stream 141 is introduced into acidic ion exchanger 200 for the removal of oxidizable impurities therefrom, as described further hereinbelow.

Stream 142 may pass through equipment that is readily available, for example, a heat exchanger or separation vessel before streams 145 or 148 recycle components of stream 142. Other streams may be included, for example, a stream may recycle a bottoms mixture of drying column 140 back into drying column 140. Any stream received by or emitted from drying column 140 may pass through a pump, compressor, heat exchanger, separation vessel, and the like as is common in the art.

The de-watered acetic acid may be introduced into a second distillation column (e.g., a heavy-ends distillation column) adapted to separate components of the acetic acid stream and form a second or heavy ends overhead stream and a second or heavy-ends bottoms stream. The second overhead stream may include methyl iodide, methyl acetate, acetic acid, water, impurities or combinations thereof. The heavy-ends column may include a distillation column and equipment associated with the distillation column including but not limited to heat exchangers, decanters, pumps, compressors, valves, and the like.

In the embodiment of FIG. 1, heavy-ends column 150 is configured to receive de-watered acetic acid process stream 141 from drying column 140. Heavy-ends column 150 may separate components from de-watered acetic acid stream 141 into heavy-ends overhead stream 152, heavy ends bottoms stream 151, and acetic acid process stream 156. Heavy-ends overhead stream 152 and heavy-ends bottoms stream 151 comprising heavy impurities such as propionic acid, may be sent to additional processing equipment for further processing. In embodiments, stream 152 may be recycled, for example, to heavy-ends column 150. Stream 156 may comprise acetic acid product.

Acetic acid process stream 156 may be subjected to an additional purification to remove organic iodide either upstream or downstream of acidic ion exchanger 200 when all or a portion thereof is being subjected to acidic ion exchange as per this disclosure. For example, as indicated in the embodiment of FIG. 1, acetic acid process stream 156 may be introduced into organic iodide removal bed or apparatus 160, and an organic iodide stream 161 comprising organic iodide removed from acetic acid process stream 156 and an organic iodide-reduced acetic acid process stream 156a' comprising a reduced amount of organic iodide than acetic acid process stream 156 removed therefrom. At least a portion of the acetic acid process stream 156a' from which the organic iodide has been removed can be introduced via stream 156a into ion exchanger 200, as further described below. In embodiments, at least a portion of acetic acid process stream 156 is introduced directly into acidic ion exchanger 200 via stream 156a. Organic iodide removal apparatus 160 may comprise apparatus configured for treating the acetic acid process stream 156 with a resin or material comprising a metal ion, e.g., a silver loaded resin having a metal loading of greater than 15 wt % to remove inorganic or organic halides, such as described in U.S. Pat. No. 9,822,055 entitled Silver Loaded Halide Removal Resins for Treating Halide Containing Solutions, the disclosure of which is hereby incorporated herein in its entirety for purposes not contrary to this disclosure.

While many processes exist for the separation of the impurities from product carboxylic acid streams, such processes can be difficult to implement, are not effective, and/or are costly. Thus, continuous efforts have been underway to improve and develop methods to separate these impurities from acetic acid. According to this disclosure, adsorption via acidic ion exchange is employed to effect separation of one or more oxidizable impurities from a product carboxylic acid (e.g., a GAA) stream comprising primarily carboxylic acid (e.g., greater than or equal to 99.5, 99.6, 99.7, 99.8 or 99.9 wt % carboxylic acid (e.g., GAA)), and ppm levels of oxidizable impurities (e.g., less than 2000 ppm oxidizable impurities) and less than 0.2, 0.15, or 0.1 wt % water. As noted hereinabove, any carbonylation system and method can be utilized to provide the carboxylic acid stream treated according to this disclosure. Any stream (or portion thereof) containing suitable levels of target impurities (e.g., oxidizable impurities and/or water as noted herein may contact the ion exchange resin to selectively reduce such impurities. However, one or more embodiments include contacting an acetic acid process stream, such as at least a portion or the entirety 141a of acetic acid process stream 141, at least a portion 156a or the entirety of acetic acid process stream 156, at least a portion or the entirety of the organic iodide-reduced acetic acid process stream 156a', or a combination thereof with the ion exchange media in acidic ion exchanger 200. Other embodiments may include contacting the entirety or a portion 152a of the heavy-ends distillation column overhead stream 152 with the ion exchange resin in acidic ion exchanger 200. In embodiments, an acetic acid process stream treated via ion exchange as per this disclosure is an at least partially purified acetic acid stream, not an intermediate stream comprising bulk methyl iodide, for example.

In embodiments, the carboxylic acid stream (e.g., the crude acetic acid stream) subjected to (e.g., final) purification via acidic ion exchange as per this disclosure is a de-watered acetic acid process stream (such as that in de-watered or 'dried' acetic acid process stream 141), a GAA product stream extracted from a purification section upstream of the ion exchanger of this disclosure (e.g., a purified GAA stream extracted from heavy-ends distillation column 150 via GAA product stream 156), a purified GAA stream extracted from organic iodide removal apparatus 160 via GAA product stream 156a', or a combination thereof. At least a portion of the de-watered acetic acid process stream 141 may be introduced into ion exchanger 200 via stream 141a, at least a portion of the acetic acid process stream 156 may be introduced into ion exchanger 200 via stream 156a, stream 156a', or a combination thereof, at least a portion of the organic iodide-reduced acetic acid process stream 156a' may be introduced into ion exchanger 200 via stream 156a' and 156a, or a combination thereof. In embodiments, regardless of the source(s) of the crude acetic acid feed(s) to ion exchanger 200, a stream 156b comprising purified acetic acid having a reduced amount of oxidizable impurities is removed from ion exchanger 200. In embodiments, purified, de-watered acetic acid from ion exchanger 200 comprising a reduced amount of oxidizable impurities is introduced into heavy-ends distillation column 150 via stream 141b, for example by re-introduction into de-watered acetic acid process stream 141, as depicted in the embodiment of FIG. 1. Thus, a variety of the acetic acid streams may be passed through ion exchanger 200 prior to proceeding downstream (e.g., prior to introduction into iodide removal apparatus 160 and/or other purification), or, in embodiments, as a final purification step. For example, stream 156 may be passed through acidic ion exchanger 200 via stream 156a to form stream 156b. Alternatively, or in combination therewith, all or a portion of stream 156 may pass through iodide removal apparatus 160, and the iodide-reduced acetic acid stream 156a' passed through adsorption bed 200 via stream 156a (or directly via stream 156a', not shown in the embodiment of FIG. 1) to form purified acetic acid product stream 156b.

Alternatively, or in combination therewith, all or a portion of stream 152 may be passed through acidic ion exchanger 200 via stream 152a to form stream 152b, which may be returned to heavy-ends distillation column 150 via, for example, stream 152. Alternatively, or in combination therewith, dried acetic acid process stream 141 may be passed through adsorption bed 200 via stream 141a to form stream 141b, which may be returned to heavy-ends distillation column 150, for example, via stream 141.

Although described with reference to the carboxylic acid production system of FIG. 1, it is to be understood that a carboxylic acid product stream purified via acidic ion exchange as per this disclosure can be the product of a variety of systems and methods operable to provide such a low water (e.g., less than 0.15 wt % water), low impurity (e.g., ppm level, for example less than 2000 ppm oxidizable impurities), high carboxylic acid (greater than or equal to 99.5 wt % carboxylic acid) content crude process stream. For example, alternative embodiments for a carboxylic acid production system 100 whereby such a carboxylic acid stream suitable for acidic ion exchange treatment according to this disclosure can be obtained may be found in U.S. Pat. Nos. 6,552,221; 7,223,886; 7,683,212; 8,940,932; 8,969,613; 9,056,825; 9,216,936; U.S. Patents Pub. No. 2016/0289153; 2016/0376213; 2017/0158592; 2017/0158596; the disclosure of each of which is hereby incorporated herein by reference for purposes not contrary to this disclosure.

The ion exchange resin comprises an acidic ion exchange resin. A wide variety of ion exchange resins may be used to remove oxidizable impurities from the acetic acid process stream according to this disclosure. One type of ion exchange resin which may be used comprises macroreticular polymeric resins. Depending on the actual mechanism of removal and the amounts of impurities, other resins such as mesoporous or gel may be employed.

The acidic ion exchange resin can comprise a macroreticular polymeric ion exchange resin, including, but not limited to, strongly acidic resins which are capable of binding cationic species. Such strongly acidic resins have acid functionalities with pKa values less than 1. For example, AMBERLYST® 15 has a sulfonic acid functionality; the pKa for para-toluene sulfonic acid is −2.8. In embodiments, the acidic ion exchange resin is a strongly acidic cation exchange resin. In embodiments, the acidic ion exchange resin is macroreticular, macroporous, mesoporous, polymeric, gel, or a combination thereof. In embodiments, the resin is a polymeric resin comprising discrete particles containing cross-linked polystyrene with divinyl benzene which contain active sites. The active sites of the resin are chemical groups in the resin which bind to agents which remove impurities from the acetic acid process stream contacted therewith. In embodiments, these chemical groups are pH sensitive and protonation or deprotonation leads to the development of a charged species. In embodiments, the active sites of the resin are strongly acidic groups such as sulfonic acids or are weakly acidic groups such as carboxylic acids. In embodiments, the acidic ion exchanger 200 can be utilized with the acid form (e.g., the $H^+$-form) of the ion exchange resin. In embodiments, the stream to be treated via ion exchange in ion exchanger 200 is not subjected to ion exchange with a metal-exchanged or otherwise functionalized form of the ion exchange resin prior (e.g., immediately prior) to, subsequent, (e.g., immediately after) or either prior to or subsequent the contact with the $H^+$-form of the ion exchange resin in ion exchanger 200.

In embodiments, the acidic ion exchange resin is selected from AMBERLYST® 15, AMBERLYST® 15-Dry, AMBERLITE™ IR120, DOWEX™ Marathon C-10 Resin, or DOWEX® DR-2030, each available from the DOW Chemical Company, PUROLITE C145, or PUROLITE CT145, each available from Purolite, or a combination thereof. In embodiments, the ion exchange resin comprises AMBERLYST™ 15.

In embodiments, the acidic ion exchange resin has a minimum number of active sites from 1 equivalent to 4 equivalents per liter, as determined by ammonia adsorption or titration. In embodiments, the minimum number of active sites is from 1.5 equivalents to 3.0 equivalents per liter. In embodiments, the acidic ion exchange resin has a concentration of active sites of greater than or equal to 0.7, 1.1 or 1.5 equivalents/kg, less than or equal to 8.0, 7.0, 6.0, 5.0, 4.3 or 1.6 equivalents/kg, or a combination thereof. In embodiments, any commercially available strongly acidic ion exchange resin is used to remove oxidizable impurities from the crude acetic acid process stream being treated.

In embodiments, the acidic ion exchange resin contains a percentage of cross-linking. In embodiments, the amount of crosslinking, as determined by the extent of swelling upon water uptake, is from 1% to 25%, such as from 2% to 15% or from 4% to 12%. In embodiments, the particle size of the ion exchange resin, as determined by techniques such as light scattering and laser diffraction, has a harmonic mean size from 0.1 mm to 4 mm, including from 0.2 mm to 2 mm and from 0.5 mm to 1 mm. In embodiments, the uniformity coefficient of the acidic ion exchange resin particles is from 1.1 to 4, such as from 1.5 to 2. In embodiments, the particle size is highly uniform and contains less than 10% of particles outside the range from 0.3 mm to 1.2 mm, including less than 5% of particles outside the range from 0.3 mm to 1.2 mm. In embodiments, it is contemplated that the size of the particles changes when exposed to solvent, water, and/or the (e.g., acetic acid) stream being treated. In embodiments, the particles exhibit swelling from the dry state to the aqueous state of greater than 25 volume percent (vol %), including greater than 35 vol %.

In embodiments, the surface area of the ion exchange resin promotes the interaction of the impurities with the active sites of the resin. In embodiments, the ion exchange resin has a surface area, as determined by BET nitrogen adsorption, of greater than or equal to 30, 40, 50, 60, 70, 80, 90 $m^2$/g, or more, less than or equal to 500, 400, 300, 200, 100, 90, 80, 70, or 60 $m^2$/g, or a combination thereof. In embodiments, the ion exchange resin has an average pore diameter, as determined by techniques such as atomic force microscopy, of greater than or equal to 10, 15, 20, 25, 30, 35, or 40 nm, less than or equal to 100, 90, 80, 75, 70, 60, or 50 nm, or a combination thereof. In embodiments, the total pore volume of the ion exchange resin is greater than or equal to 0.2, 0.3, or 0.4 mL/g, less than or equal to 0.7, 0.6, or 0.5 mL/g, or a combination thereof.

For example, AMBERLYST™ 15 or AMBERLYST™ 15Dry is a bead form, strongly acidic ion exchange resin developed particularly for heterogeneous acid catalysis of a wide variety of organic reaction. It is available from The Dow Chemical Company and its subsidiary Rohm and Haas LLC, Philadelphia, Pa., USA. AMBERLYST™ 15Dry may be manufactured as opaque beads and may have a macroreticular pore structure with hydrogen ion sites located throughout each bead. The surface area may be 53 $m^2$/g, the average pore diameter may be 300 angstroms, and the total pore volume may be 0.40 cc/g. AMBERLYST™ 15Dry may be utilized in essentially non-aqueous systems (e.g., less than 1 wt % water). Therefore, the solution may be essentially or substantially nonaqueous with use of AMBERLYST™ 15Dry.

According to this disclosure at least a portion of the carboxylic acid process stream is contacted with an acidic ion exchange resin, as described above, at conditions sufficient to selectively decrease the concentration of one or more impurities present in the carboxylic acid process stream. As used herein, the term "selectively reduce" refers to the reduction in concentration of one or more target components (i.e., oxidizable impurities) without substantial (e.g., greater than 0.5 wt %) reduction in the concentration of acetic acid present in the stream.

In embodiments, the crude carboxylic acid process stream (e.g., the GAA process stream 141, 156, 156a') contacted with the acidic ion exchange resin as per this disclosure comprises one or more oxidizable compounds, at a concentration of less than or equal to 2000, 1000, or 750 ppm based on the total weight of the carboxylic acid process stream. In embodiments, the carboxylic acid process stream contacted with the acidic ion exchange resin as per this disclosure comprises water at a concentration in a range of from 0 wt % to 0.2 wt %, from 0 wt % to 0.15 wt %, or less than or equal to 0.2, 0.15, or 0.1 wt %, based on the total weight of the carboxylic acid process stream. In embodiments, the carboxylic acid process stream contacted with the acidic ion exchange resin as per this disclosure is essentially anhydrous (e.g., comprises less than 0.2 wt % water). In embodiments, the oxidizable impurities in the crude acetic acid product include from 0 ppm to 200 ppm, from 100 ppm to 200 ppm, or from 150 ppm to 200 ppm oxidizable impurities, based on the total weight of the crude acetic acid product.

At least a portion of the crude carboxylic acid process stream contacts the acidic ion exchange resin under conditions sufficient to reduce the concentration of one or more oxidizable impurities present in the carboxylic acid process stream. For example, the concentration of one or more of the oxidizable impurities may be reduced by at least 50 wt %, or at least 80 wt %, or at least 85 wt %, or at least 90 wt %, or at least 95 wt %, or at least 98 wt %. In embodiments, a concentration of oxidizable impurities in the purified acetic acid product is decreased by at least 30, 40, 50, 60, 70, 80, 85, 90, 95, or 98% relative to a concentration of oxidizable impurities in the crude acetic acid product. In embodiments, the purified carboxylic acid stream (e.g., the purified GAA stream resulting from acidic ion exchange 141b, 156b) comprises less than or equal to 100, 50 or 10 ppm oxidizable impurities, based on a total weight of the purified acetic acid product. In embodiments, the purified acetic acid product comprises less than or equal to 0.2, 0.15 or 0.1 wt % water, based on a total weight of the purified acetic acid product.

In embodiments, the purified acetic acid product has a permanganate time measured by a number of crotonaldehyde equivalents therein as determined via UV/Vis as described in U.S. Pat. No. 8,293,534 (which is hereby incorporated herein by reference in its entirety for purposes not contrary to this disclosure) and summarized hereinbelow, that is improved by at least 25%, 45%, or 65% relative to that of the crude acetic acid.

The UV/Vis method for quantifying the PRC content, otherwise known as oxidizable impurity content, of an acetic acid sample may comprise: (a) establishing a correlation between permanganate absorbances of standard samples and their PRC content by: (i) preparing two or more standard samples with known PRC contents; (ii) adding a known amount of a standard permanganate solution to each standard sample from (a)(i) to form a mixture; (iii) for each standard sample, measuring the absorbance of the mixture ($A_{mix}$) at a selected wavelength in the range of 460 to 580 nm at a set reaction time; (iv) for each standard sample, determining the permanganate absorbance ($A_{perm}$) at the set reaction time by subtracting from $A_{mix}$, the absorbance due to manganese dioxide ($A_{MnO2}$) at the selected wavelength; (v) establishing a correlation between permanganate absorbances and their PRC contents; and (b) repeating steps (a)(ii) through (a)(iv) with the unknown acetic acid sample that contains an unknown amount of PRC to determine its PRC content. In embodiments, $A_{MnO2}$ is determined by drawing a baseline across the base of a permanganate absorption band. The correlation can be a calibration curve, in embodiments. In embodiments, a solvent can be utilized to form the mixture. Such a solvent can be selected from water, alcohols, carboxylic acids, amides, nitriles, or a combination thereof. The standard permanganate solution can, in embodiments, be a potassium permanganate solution. The set reaction time can, in embodiments, be in a range from 10 to 30 minutes.

At least a portion of the carboxylic acid process stream to be subjected to ion exchange as per this disclosure may contact the ion exchange resin via methods available in the relevant literature. For example, the ion exchange resin may be disposed as a bed in a column and the at least a portion of the carboxylic acid product may pass through the bed to reduce the concentration of one or more components/impurities therein. The ion exchange resin may be disposed in the fixed bed by manners available in the relevant literature. In embodiments, the carboxylic acid product to be treated via ion exchange as per this disclosure is passed through an ion exchange column at a flow rate in the range of from 0.1 to 50 bed volumes per hour (BV/h), from 1 to 40 BV/h, or from 5 to 30 BV/h, wherein a flow rate of 1 BV/h means that a quantity of crude acetic acid product equal to a volume occupied by the fixed bed of the acidic ion exchange resin passes through the fixed bed in one hour.

The ion exchange resin may be loaded in the bed in an amount in a range of 1 g ion exchange resin per 2-15 grams of carboxylic acid product to be treated, or 1 g ion exchange resin per 5-15 grams of carboxylic acid product to be treated, or 1 g ion exchange resin per 5-10 grams of carboxylic acid product to be treated. In embodiments, the contacting comprises batch mode contacting in a static slurry. In embodiments, a mass ratio of carboxylic acid stream to be treated to the acidic ion exchange resin in the slurry is in the range of from 1 to 25 grams of carboxylic acid stream per gram of resin.

The ion exchange conditions vary depending upon numerous factors. In embodiments, the acetic acid process stream to be treated is exposed to the ion exchange resin bed at an elevated temperature, i.e., above room temperature. In embodiments, the ion exchange temperature is in a range of from 30° C. to 150° C., from 40° C. to 120° C., from 40° C. to 100° C., or greater than or equal to 40° C., 50° C., 60° C., 70° C., 80° C., 90° C., or 100° C. As used herein, "room temperature" means that a temperature difference of a few degrees does not matter to the phenomenon under investigation. In some environments, room temperature may include a temperature in a range of 20° C. to 28° C., while in other environments, room temperature may include a temperature in a range of 10° C. to 32° C., for example. However, room temperature measurements may not include close monitoring of the temperature of the process and therefore such a recitation does not intend to bind the embodiments described herein to any predetermined temperature range.

In embodiments, a contact time of the carboxylic acid product to be treated with the acidic ion exchange resin is in the range of from 10 minutes to 3 hours, from 5 minutes to 2 hours, or from 1 minute to 1 hour. The contact time may comprise a time of contact for static contact, a residence time for passage of the carboxylic acid stream to be treated through the ion exchange column, or the like. As will be appreciated by one of skill in the art, an enhanced residence or contact time of the impurity-containing acetic acid stream with the ion exchange resin may provide for enhanced impurity removal via the ion exchange resin. Thus, a slower flow rate through a flow-through resin bed, an increased contact time for a static slurry bed of resin, an increased amount of active sites per impurity level to be removed, and the like, can enhance removal of the impurities via the ion exchange resin.

It is contemplated that other reaction conditions and characteristics of the ion exchange resin affect the ability of the resin to bind impurities, which can assist in the removal of such impurities from a solution. Without undue experimentation, these reaction conditions and characteristics may be optimized by a skilled artisan.

It is contemplated that the ion exchanger may occasionally undergo regeneration or replacement. The regeneration procedure may include any regeneration procedure available in the relevant literature. The ion exchange resin may be regenerated either in the adsorbent bed or slurry contact vessel may be removed from the ion exchange column or vessel for regeneration. Such regeneration is known to the skilled artisan. However, a non-limiting illustrative embodiment of in-line regeneration is described below.

In a non-limiting example of in-line regeneration, the ion exchanger is initially taken off-line and the ion exchange bed disposed therein is drained. The ion exchange resin may then undergo a regeneration step. The regeneration conditions may be any conditions that are effective for at least partially reactivating the ion exchange media and are generally known to one skilled in the art. For example, regeneration may include passing a high salt solution (e.g., 1 M NaCl) through the column (e.g., in the opposite direction of service operation) until impurities are eluted therefrom, and/or may include processing the spent adsorbent at room temperature or at high temperatures. During regeneration, the adsorbed components (e.g., crotonaldehyde) are desorbed and discharged from ion exchanger 200. The desorbed components may be recovered or disposed as waste.

In order to minimize disruption to the process during periods of regeneration or replacement, one or more embodiments of the present disclosure utilize swing beds for the adsorption of one or more acetic acid processing impurities. In such embodiments, continuous operation can be achieved. For example, one ion exchange bed may be taken off-line for potential removal and/or regeneration of the ion exchange medium therein, while the remaining ion exchange bed may remain on-line for production.

The herein-disclosed system and method may enable the purification of carboxylic acid process streams containing low levels (e.g., ppm levels) of oxidizable impurities/PRCs, in a simple and economical manner. Utilizing a readily available and cost effective ion exchange resin for removal of low levels of impurities from carboxylic acid product streams can provide purified carboxylic acid streams having acceptable levels of oxidizable impurities for downstream end uses (such as, without limitation, the production of vinyl acetate from acetic acid and ethylene, wherein acetaldehyde and impurities derived therefrom can degrade palladium catalysts).

In embodiments, the permanganate time (oxidizable impurity content) of a GAA product can be improved by contact with an acidic ion exchange resin (e.g., AMBERLYST® 15 or AMBERLYST® 15Dry) at elevated temperatures (e.g., greater than or equal to 70° C.). Surprisingly, many other materials, such as zeolites and carbons, provide little to no improvement in PT in this regard. In embodiments, the contact with the acidic ion exchange resin is performed in an essentially non-aqueous (e.g., less than or equal to 0.2 wt % water) environment.

The following examples merely illustrate the system and method of this disclosure. Those skilled in the art will recognize many variations that are within the spirit of this disclosure and the scope of the claims.

EXAMPLES

To facilitate a better understanding of the disclosure, the following examples of embodiments are given. In no way should the following examples be read to limit, or to define, the scope of the appended claims.

Example 1: Room Temperature Experiments

A sample of GAA product obtained from a methanol carbonylation facility operating in continuous mode was contacted for 1 hour at room temperature with various materials, including acidic and non-acidic zeolites, silicoaluminophosphates (SAPOs), molecular sieves, activated carbons and cationic resins. For these tests, 1 gram of material was contacted with 8 grams of GAA in a static vial for one hour at 20° C. prior to post-treatment sampling. The permanganate time (PT) or oxidizable impurity content of pre- and post-treated GAA was determined using Lyondell's proprietary UV-Vis method, as described in U.S. Pat. No. 8,293,534.

The data in Table 1 indicate that no removal of oxidizable impurities was achieved at room temperature. In fact, in some instances, a worsening of PT was observed. Without wishing to be limited by theory, this worsening may have resulted from the leaching of oxidizable materials from the surface of the material.

TABLE 1

| Sample | Material | Crotonaldehyde Equivalents |
|---|---|---|
| Blank | None | 1.0 |
| GAA | None | 12.2 |
| GAA | None | 12.3 |
| GAA | SAPO-34 | 13.1 |
| GAA | SAPO-11 | 14.1 |
| GAA | ZSM-5-H-26 | 10.6 |
| GAA | ZSM-5-H-371 | 11.5 |
| GAA | Zeolite HY | 12.1 |
| GAA | Zeolite NaY | 13.0 |
| GAA | MCM-22 | 15.6 |
| GAA | PUROLITE ® MN500 | 18.8 |
| GAA | NORIT ® Carbon 07561 | 16.3 |
| GAA | NORIT ® Carbon 12x20 U | 12.8 |
| GAA | NORIT ® Carbon ROX 0.8 | 13.0 |
| GAA | NORIT ® Carbon GAC 12407 | 13.0 |
| GAA | AMBERLYST ® 15 | 12.8 |
| GAA | AMBERLITE ® IR120 | 14.0 |
| GAA | Molecular Sieves | 11.9 |

Example 2: Elevated Temperature Experiments

A different picture emerges at 60° C., as shown in Table 2. For these experiments, 1 gram of material was combined with 8 grams of sample in a static vial in a 60° C. bath, and sampled periodically as indicated in Table 2. When the GAA product was contacted for a contact time of 2.5 hours with AMBERLYST® 15, a 66% improvement in permanganate time was observed. Similar contact with an acidic nanozeolite showed no improvement. In contrast, contact with a crotonaldehyde standard in 100% aqueous solution showed almost complete removal of impurities by the nanozeolite, while there was little removal by AMBERLYST® 15. Thus, this indicates that there is both a solvent and a material dependence on removal of oxidizable impurities.

TABLE 2

| Sample | Material | Time, min | Crotonaldehyde Equivalents |
|---|---|---|---|
| GAA + 9.7 ppm Cr.* | None | N/A | 20.6 |
| GAA + 9.7 ppm Cr. | AMBERLYST ® 15 | 21 | 17.5 |
| GAA + 9.7 ppm Cr. | AMBERLYST ® 15 | 104 | 11.7 |
| 20 ppm Cr. Standard in H$_2$O | None | N/A | 18.8 |
| 20 ppm Cr. Standard in H$_2$O | AMBERLYST ® 15 | 26 | 18.6 |
| 20 ppm Cr. Standard in H$_2$O | ZSM-5-H-26 | 42 | 2.2 |
| GAA | None | N/A | 12.2 |
| GAA | AMBERLYST ® 15 | 18.5 | 10.4 |
| GAA | AMBERLYST ® 15 | 53 | 8.0 |
| GAA | AMBERLYST ® 15 | 103 | 5.9 |
| GAA | AMBERLYST ® 15 | 153 | 4.5 |
| GAA | ZSM-5-H-26 | 32 | 12.6 |
| GAA | ZSM-5-H-26 | 148 | 12.4 |

*Cr. = Crotonaldehyde

Figure 2:
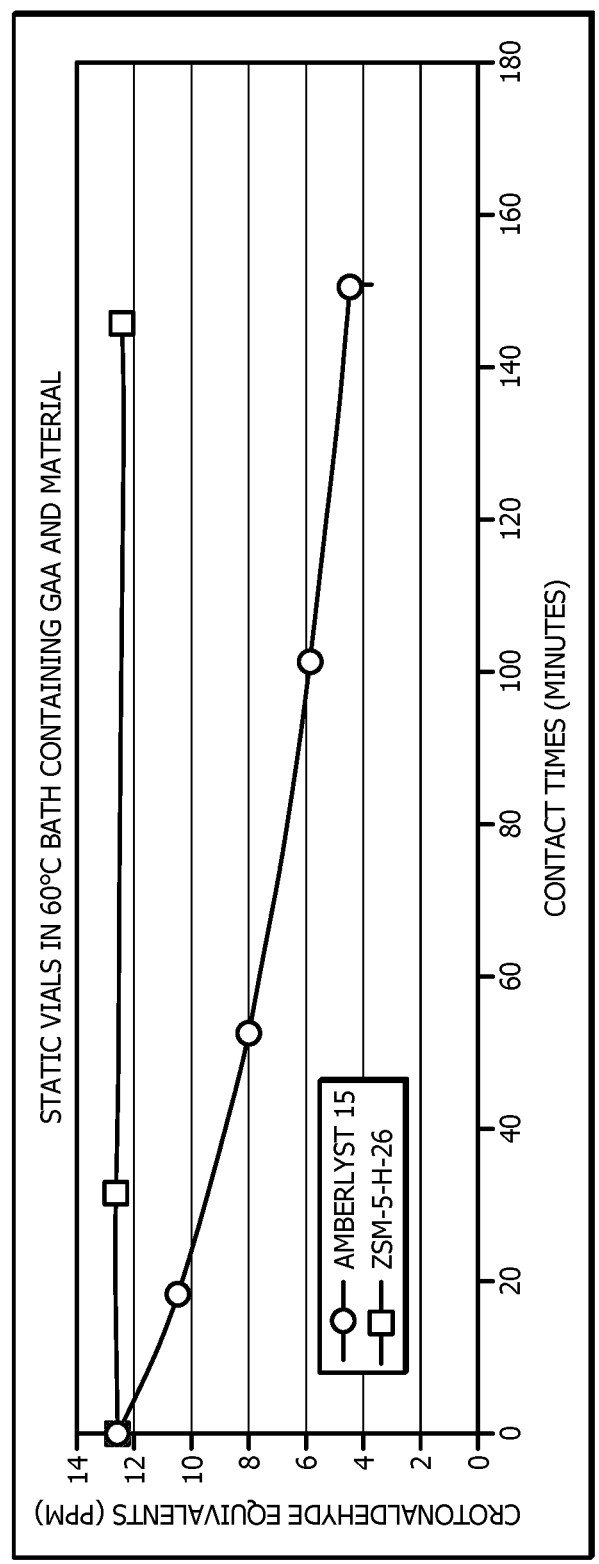
FIG. 2 is a plot of remaining crotonaldehyde equivalents as a function of contact time for experiments in Example 2.

FIG. 2 is a plot of crotonaldehyde equivalents (ppm) as a function of contact time (min) for some of the data in Table 2. These data indicate that the readily available and inexpensive AMBERLYST® can dramatically improve product purity without the capital and operationally intensive methods conventionally utilized to remove oxidizable impurities from GAA product.

Figure 3:
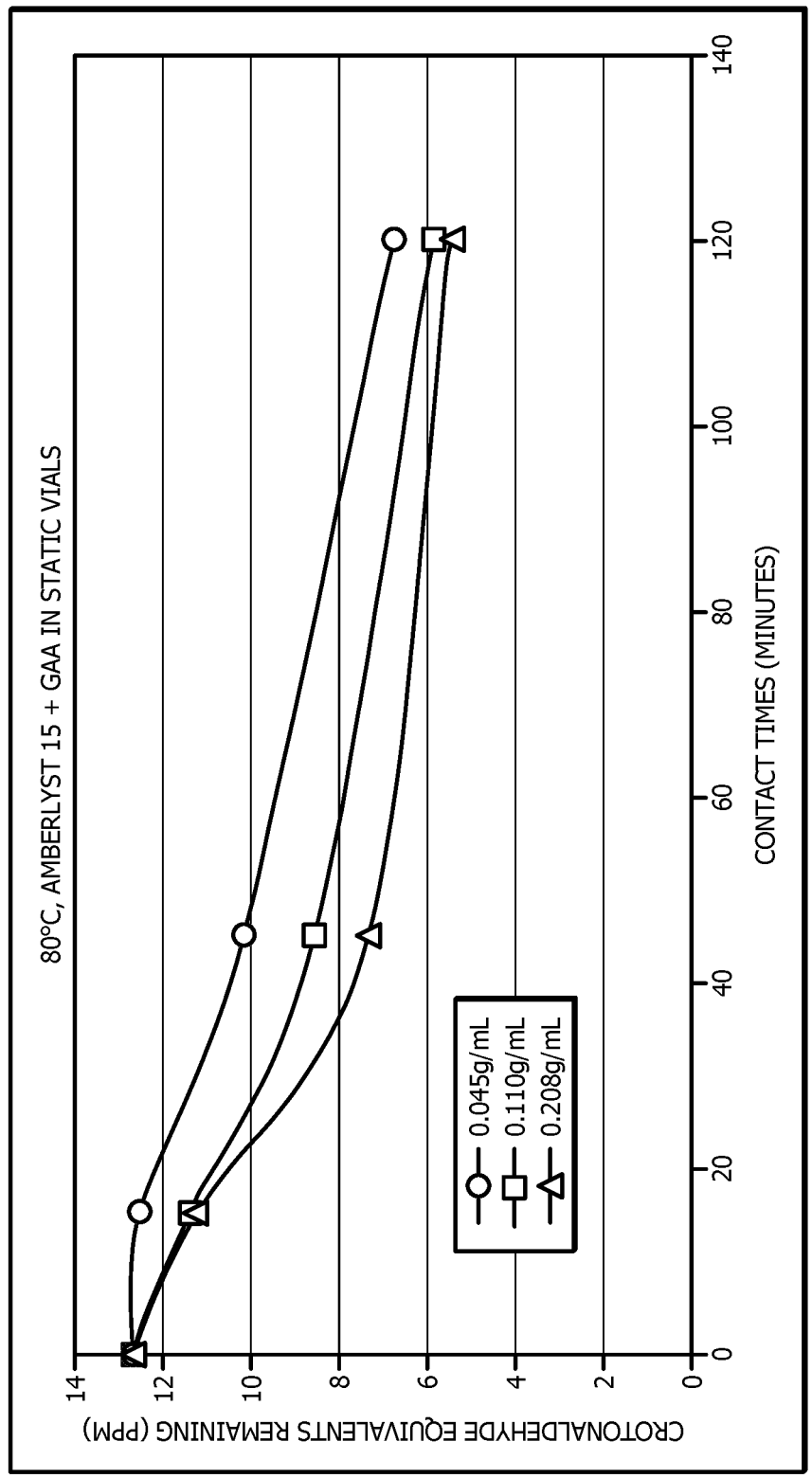
FIG. 3 is a plot of remaining crotonaldehyde equivalents as a function of contact time for additional experiments in Example 2.

Additional experiments were conducted at 80° C. These sample runs were carried out at 3 different loadings: 1 g of AMBERLYST® 15 per 22 g of acetic acid (0.045 g/mL), 1 g of AMBERLYST® 15 per 9 g of acetic acid (0.110 g/mL), and 1 g of AMBERLYST® 15 per 5 g of acetic acid (0.208 g/mL). The results are shown in FIG. 3, which is a plot of remaining crotonaldehyde equivalents (ppm) as a function of contact time (min). As seen in FIG. 3, after 2 hours, approximately half of the oxidizable impurities have been removed, with little dependence on loading. This is a similar extent of removal as was seen at 60° C. at the 2 hour mark.

Additional Disclosure

The particular embodiments disclosed above are merely illustrative, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and unambiguously defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A method comprising: contacting methanol with carbon monoxide in the presence of a liquid reaction medium under carbonylation conditions to form a carbonylation product comprising acetic acid; separating the carbonylation product into a liquid fraction and a vapor fraction comprising a majority of the acetic acid in the carbonylation product; removing, from the vapor fraction, water, light ends having a boiling point less than that of acetic acid, heavy ends having a boiling point greater than that of acetic acid, or a combination thereof, to yield a crude acetic acid product comprising at least 99.5, 99.7, or 99.9 wt % acetic acid, less than or equal to 0.2, 0.15, or 0.1 wt % water, and less than or equal to 2000, 1000, or 750 ppm oxidizable impurities, based on the total weight of the crude acetic acid product; and contacting the crude acetic acid product with an acidic ion exchange resin to provide a purified acetic acid product comprising less than 100, 50, or 10 ppm oxidizable impurities.

B: A method of removing oxidizable impurities from a crude acetic acid comprising greater than or equal to 99.5, 99.7, or 99.9 weight percent (wt %) acetic acid, less than or equal to 0.2, 0.15, or 0.1 wt % water, and from 10 to 2000, from 50 to 2000, or from 100 to 2000 ppm oxidizable impurities, the method comprising: contacting the crude acetic acid with a strongly acidic ion exchange resin to produce a purified acetic acid comprising less than or equal to 100, 50, or 10 ppm oxidizable impurities.

C: A system for producing acetic acid, the system comprising: a carbonylation reactor for contacting methanol with carbon monoxide in the presence of a liquid reaction medium under carbonylation conditions to form a carbonylation product comprising acetic acid; a flash vessel operable to separate the carbonylation product into a liquid fraction and a vapor fraction comprising a majority of the acetic acid in the carbonylation product; one or more separation apparatus configured for removing, from the vapor fraction, water, light ends having a boiling point less than that of acetic acid, heavy ends having a boiling point greater than that of acetic acid, or a combination thereof, to yield a crude acetic acid product comprising at least 99.5, 99.7, or 99.9 wt % acetic acid, less than or equal to 0.2, 0.15, or 0.1 wt % water, and less than 2000, 1000, or 750 ppm oxidizable impurities; and an ion exchange column comprising an acidic ion exchange resin, located downstream of the one or more separation apparatus, and operable to reduce an amount of the oxidizable impurities in the crude acetic acid product by at least 30, 40, 50, 60, 70, 80, 85, 90, 95, or 98% and provide a purified acetic acid product comprising less than 100, 50, or 10 ppm oxidizable impurities.

Each of embodiments A, B and C may have one or more of the following additional elements: Element 1: wherein the liquid reaction medium comprises: a carbonylation catalyst selected from rhodium catalysts, iridium catalysts and palladium catalysts; and water at a concentration in a range of from 1 wt % to 14 wt %, based on the total weight of the liquid reaction medium. Element 2: wherein the purified acetic acid product has a permanganate time measured by a number of crotonaldehyde equivalents therein, as determined via UV/Vis as described in U.S. Pat. No. 8,293,534, that is improved by at least 25%, 45%, or 65% relative to that of the crude acetic acid. Element 3: wherein contacting the crude acetic acid product with the acidic ion exchange resin comprises passing the crude acetic acid product through a fixed bed of the acidic ion exchange resin to selectively remove impurities therefrom. Element 4: wherein the contacting comprises passing the crude acetic acid product through the fixed bed at a flow rate in the range of from 0.1 to 50 bed volumes per hour (BV/h), from 1 to 40 BV/h, or from 5 to 30 BV/h, wherein a flow rate of 1 BV/h means that a quantity of crude acetic acid product equal to a volume occupied by the fixed bed of the acidic ion exchange resin passes through the fixed bed in one hour. Element 5: wherein the contacting comprises batch mode contacting in a static slurry, and wherein a mass ratio of the crude acetic acid stream to the acidic ion exchange resin is in the range of from 1 to 25 g crude acetic acid stream per gram of resin. Element 6: wherein a contact time of the crude acetic acid product with the acidic ion exchange resin is in the range of from 10 minutes to 3 hours, from 5 minutes to 2 hours, or from 1 minute to 1 hour. Element 7: wherein the acidic ion exchange resin is macroreticular, macroporous, mesoporous, polymeric, gel, or a combination thereof. Element 8: wherein the acidic ion exchange resin comprises active sites selected from strong acid groups such as sulfonic acid groups, weak acid groups such as carboxylic acid groups, or a combination thereof. Element 9: wherein the acidic ion exchange resin is a strongly acidic cation exchange resin. Element 10: wherein the acidic ion exchange resin has a surface area of greater than or equal to 30, 40, 50, 60, 70, 80, or 90 $m^2/g$, less than or equal to 500, 400, 300, 200, 100, 90, 80, 70, or 60 $m^2/g$, or a combination thereof. Element 11: wherein the acidic ion exchange resin has an average pore diameter of greater than or equal to 10, 15, 20, 25, 30, 35, or 40 nm, less than or equal to 100, 90, 80, 75, 70, 60, or 50 nm, or a combination thereof. Element 12: wherein the acidic ion exchange resin has a total pore volume of greater than or equal to 0.2, 0.3, or 0.4 mL/g, less than or equal to 0.7, 0.6, or 0.5 mL/g, or a combination thereof. Element 13: wherein the acidic ion exchange resin has a concentration of active sites of greater than or equal to 0.7, 1.1 or 1.5 equivalents/kg, less than or equal to 7.0, 4.3 or 1.6 equivalents/kg, or a combination thereof. Element 14: wherein the oxidizable impurities comprise saturated carbonyl compounds, unsaturated carbonyl compounds, aldol condensation products thereof, propionic acid, or combinations thereof. Element 15: wherein the oxidizable impurities comprise acetaldehyde, acetone, methyl ethyl ketone, butyraldehyde, crotonaldehyde, 2-ethyl crotonaldehyde, 2-ethyl butyraldehyde, aldol condensation products thereof, propionic acid, or combinations thereof. Element 16: wherein removing, from the vapor fraction, water, light ends having a boiling point less than that of acetic acid, heavy ends having a boiling point greater than that of acetic acid, or a combination thereof comprises removing, from the vapor fraction, an overhead comprising light ends having a boiling point less than that of acetic acid, and a side draw acetic acid stream via a light ends distillation column. Element 17: wherein removing, from the vapor fraction, water, light ends having a boiling point less than that of acetic acid, heavy ends having a boiling point greater than that of acetic acid, or a combination thereof further comprises drying the side draw acetic acid stream to reduce a water content thereof, thus providing a dried acetic acid stream. Element 18: wherein the side draw acetic acid stream comprises greater than or equal to 2, 5, or 10 wt % water, and the dried acetic acid stream comprise less than or equal to 5000, 1000, or 500 ppm water. Element 19: wherein removing, from the vapor fraction, water, light ends having a boiling point less than that of acetic acid, heavy ends having a boiling point greater than that of acetic acid, or a combination thereof further comprises removing, from the dried acetic acid stream, the crude acetic acid product and a bottoms stream comprising heavy ends having a boiling point greater than that of acetic acid via a heavy ends distillation column. Element 20: wherein the crude acetic acid product comprises from 0 ppm to 200 ppm, from 100 ppm to 200 ppm, or from 150 ppm to 200 ppm oxidizable impurities, based on the total weight of the crude acetic acid product. Element 21: wherein a concentration of oxidizable impurities in the purified acetic acid product is decreased by at least 30, 40, 50, 60, 70, 80, 85, 90, 95, or 98% relative to a concentration of oxidizable impurities in the crude acetic acid product. Element 22: wherein the purified acetic acid product comprises less than or equal to 100, 35 or 10 ppm oxidizable impurities, based on a total weight of the purified acetic acid product. Element 23: wherein the purified acetic acid product comprises less than or equal to 0.2, 0.15 or 0.1 wt % water, based on a total weight of the purified acetic acid product. Element 24: wherein the contacting of the crude acetic acid with the acidic ion exchange resin is performed at a temperature of greater than or equal to 40° C., 50° C., 60° C., 70° C., 80° C., 90° C., or 100° C. Element 25: wherein the vapor fraction, the crude acetic acid product, or both comprise less than or equal to 1, 5, or 50 ppm lithium. Element 26: wherein the contacting of the crude acetic acid product with the acidic ion exchange resin to provide the purified acetic acid product is a final purification step of the method. Element 27: wherein the oxidizable impurities are selected from acetaldehyde, acetone, methyl ethyl ketone, butyraldehyde, crotonaldehyde, 2-ethyl crotonaldehyde, 2-ethyl butyraldehyde, aldol condensation products thereof, or combinations thereof. Element 28: wherein the contacting is performed at a temperature of at least 40° C., 50° C., 60° C., 70° C., 80° C., 90° C., or 100° C. Element 29: wherein the contacting of the crude acetic acid with the strongly acidic ion exchange resin is a final purification step of the method. Element 30: wherein the ion exchange column is a final purification apparatus of the system for producing acetic acid. Element 31: wherein the one or more separation apparatus comprises a light ends distillation column configured to recover, from the vapor fraction, an overhead comprising light ends having a boiling point less than that of acetic acid and a side draw acetic acid stream. Element 32: wherein the one or more separation apparatus further comprises a dryer configured to reduce a water content of the side draw acetic acid stream to provide a dried acetic acid stream. Element 33: wherein the one or more separation apparatus further comprises a heavy ends distillation column configured to separate, from the dried acetic acid stream, the crude acetic acid product and a bottoms heavy ends stream having a boiling point greater than that of acetic acid. Element 34: not comprising a lithium removal apparatus configured for the removal of lithium.

While certain embodiments have been shown and described, modifications thereof can be made by one skilled in the art without departing from the teachings of this disclosure.

Numerous other modifications, equivalents, and alternatives, will become apparent to those skilled in the art once the above disclosure is fully appreciated. It is intended that the following claims be interpreted to embrace such modifications, equivalents, and alternatives where applicable. Accordingly, the scope of protection is not limited by the description set out above but is only limited by the claims which follow, that scope including equivalents of the subject matter of the claims.

What is claimed is:

1. A method comprising:
    contacting methanol with carbon monoxide in the presence of a liquid reaction medium under carbonylation conditions to form a carbonylation product comprising acetic acid;
    separating the carbonylation product into a liquid fraction and a vapor fraction comprising a majority of the acetic acid in the carbonylation product;
    removing, from the vapor fraction, water, light ends having a boiling point less than that of acetic acid, heavy ends having a boiling point greater than that of acetic acid, or a combination thereof, to yield a crude acetic acid product comprising at least 99.5 weight percent (wt %) acetic acid, less than or equal to 0.2 wt % water, and less than or equal to 2000 ppm oxidizable impurities, based on the total weight of the crude acetic acid product; and
    contacting the crude acetic acid product with an acidic ion exchange resin to provide a purified acetic acid product comprising less than 100 ppm oxidizable impurities.

2. The method of claim 1, wherein the purified acetic acid product has a permanganate time measured by a number of crotonaldehyde equivalents therein that is improved by at least 25% relative to that of the crude acetic acid.

3. The method of claim 1, wherein the acidic ion exchange resin is macroreticular, macroporous, mesoporous, polymeric, gel, or a combination thereof.

4. The method of claim 1, wherein the acidic ion exchange resin comprises active sites selected from strong acid groups, weak acid groups, or a combination thereof.

5. The method of claim 1, wherein the oxidizable impurities comprise saturated carbonyl compounds, unsaturated carbonyl compounds, aldol condensation products thereof, propionic acid, or combinations thereof.

6. The method of claim 5, wherein the oxidizable impurities comprise acetaldehyde, acetone, methyl ethyl ketone, butyraldehyde, crotonaldehyde, 2-ethyl crotonaldehyde, 2-ethyl butyraldehyde, aldol condensation products thereof, propionic acid, or combinations thereof.

7. The method of claim 1, wherein removing, from the vapor fraction, water, light ends having a boiling point less than that of acetic acid, heavy ends having a boiling point greater than that of acetic acid, or a combination thereof comprises removing, from the vapor fraction, an overhead comprising light ends having a boiling point less than that of acetic acid, and a side draw acetic acid stream via a light ends distillation column.

8. The method of claim 7, wherein removing, from the vapor fraction, water, light ends having a boiling point less than that of acetic acid, heavy ends having a boiling point greater than that of acetic acid, or a combination thereof further comprises drying the side draw acetic acid stream to reduce a water content thereof, thus providing a dried acetic acid stream.

9. The method of claim 8, wherein the side draw acetic acid stream comprises greater than or equal to 2 wt % water, and the dried acetic acid stream comprise less than or equal to 5000 ppm water; wherein removing, from the vapor fraction, water, light ends having a boiling point less than that of acetic acid, heavy ends having a boiling point greater than that of acetic acid, or a combination thereof further comprises removing, from the dried acetic acid stream, the crude acetic acid product and a bottoms stream comprising heavy ends having a boiling point greater than that of acetic acid via a heavy ends distillation column; or a combination thereof.

10. The method of claim 1, wherein the contacting of the crude acetic acid with the acidic ion exchange resin is performed at a temperature of greater than or equal to 40° C., wherein the contacting of the crude acetic acid product with the acidic ion exchange resin to provide the purified acetic acid product is a final purification step of the method, or both.

11. A method of removing oxidizable impurities from a crude acetic acid comprising greater than or equal to 99.5 weight percent (wt %) acetic acid, less than or equal to 0.2, wt % water, and from 10 to 2000 ppm oxidizable impurities, the method comprising:
    contacting the crude acetic acid with a strongly acidic ion exchange resin to produce a purified acetic acid comprising less than or equal to 100 ppm oxidizable impurities.

12. The method of claim 11, wherein the oxidizable impurities are selected from acetaldehyde, acetone, methyl ethyl ketone, butyraldehyde, crotonaldehyde, 2-ethyl crotonaldehyde, 2-ethyl butyraldehyde, aldol condensation products thereof, or combinations thereof.

13. The method of claim 11, wherein the contacting is performed at a temperature of at least 40° C., wherein the contacting of the crude acetic acid with the strongly acidic ion exchange resin is a final purification step of the method, or both.

14. A system for producing acetic acid, the system comprising:
    a carbonylation reactor for contacting methanol with carbon monoxide in the presence of a liquid reaction medium under carbonylation conditions to form a carbonylation product comprising acetic acid;
    a flash vessel operable to separate the carbonylation product into a liquid fraction and a vapor fraction comprising a majority of the acetic acid in the carbonylation product;
    one or more separation apparatus configured for removing, from the vapor fraction, water, light ends having a boiling point less than that of acetic acid, heavy ends having a boiling point greater than that of acetic acid, or a combination thereof, to yield a crude acetic acid product comprising at least 99.5 weight percent (wt %) acetic acid, less than or equal to 0.2 wt % water, and less than 2000 ppm oxidizable impurities; and an ion exchange column comprising an acidic ion exchange resin, located downstream of the one or more separation apparatus, and operable to reduce an amount of the oxidizable impurities in the crude acetic acid product by at least 30% and provide a purified acetic acid product comprising less than 100 ppm oxidizable impurities.

15. The system of claim 14, wherein the ion exchange column is a final purification apparatus of the system for producing acetic acid.

16. The system of claim 14, wherein the acidic ion exchange resin is macroreticular, macroporous, mesoporous, polymeric, gel, or a combination thereof.

17. The system of claim 14, wherein the acidic ion exchange resin comprises active sites selected from strong acid groups, weak acid groups, or a combination thereof.

18. The system of claim 14, wherein the oxidizable impurities are selected from acetaldehyde, acetone, methyl ethyl ketone, butyraldehyde, crotonaldehyde, 2-ethyl crotonaldehyde, 2-ethyl butyraldehyde, aldol condensation products thereof, or combinations thereof.

19. The system of claim 14, wherein the one or more separation apparatus comprises a light ends distillation column configured to recover, from the vapor fraction, an overhead comprising light ends having a boiling point less than that of acetic acid and a side draw acetic acid stream; wherein the one or more separation apparatus further comprises a dryer configured to reduce a water content of the side draw acetic acid stream to provide a dried acetic acid stream; or both.

20. The system of claim 19, wherein the side draw acetic acid stream comprises greater than or equal to 2 wt % water, and the dried acetic acid stream comprises less than or equal to 5000 ppm water; wherein the one or more separation apparatus further comprises a heavy ends distillation column configured to separate, from the dried acetic acid stream, the crude acetic acid product and a bottoms heavy ends stream having a boiling point greater than that of acetic acid; or both.

* * * * *